United States Patent
Belleau et al.

Patent Number: 5,587,480
Date of Patent: Dec. 24, 1996

[54] SUBSTITUTED 1,3-OXATHIOLANES AND SUBSTITUTED 1,3-DITHIOLANES WITH ANTIVIRAL PROPERTIES

[75] Inventors: Bernard Belleau, deceased, late of Westmount, by Pierrette Belleau, executrix; Nghe Nguyen-Ba, La Prairie; Laval C. C. Kong, Kirkland; Tarek Mansour, Montreal; Haolun Jin, Pierrefonds, all of Canada; Livio Brasili, Modena, Italy

[73] Assignee: BioChem Pharma, Inc., Laval, Canada

[21] Appl. No.: 230,317

[22] Filed: Apr. 20, 1994

Related U.S. Application Data

[63] Continuation-in-part of Ser. No. 791,441, Nov. 13, 1991, abandoned, which is a continuation-in-part of Ser. No. 612,840, Nov. 13, 1990, abandoned.

[51] Int. Cl.$^6$ .......................... C07D 239/02; A61K 31/505
[52] U.S. Cl. .......................... 544/310; 544/300; 544/316; 544/317; 544/318
[58] Field of Search ..................... 544/300, 310, 544/316–318; 514/269, 274

[56] References Cited

U.S. PATENT DOCUMENTS

| | | | |
|---|---|---|---|
| 4,000,137 | 12/1976 | Dvonch | 260/252 |
| 4,336,381 | 6/1982 | Nagata | 544/313 |
| 5,039,667 | 8/1991 | Tyrrell | 514/45 |
| 5,118,672 | 6/1992 | Schinazi et al. | 514/47 |
| 5,159,067 | 10/1992 | Schinazi et al. | 536/27 |

FOREIGN PATENT DOCUMENTS

| | | |
|---|---|---|
| 0212409 | 3/1987 | European Pat. Off. . |
| 0337713 | 1/1989 | European Pat. Off. . |
| 0349242 | 1/1990 | European Pat. Off. . |
| 0363582 | 4/1990 | European Pat. Off. . |
| 0382526 | 8/1990 | European Pat. Off. . |
| 515157 | 11/1992 | European Pat. Off. . |
| 515156 | 11/1992 | European Pat. Off. . |
| 2063257 | 6/1981 | United Kingdom . |
| 2230266 | 10/1990 | United Kingdom . |
| WO88/08001 | 10/1988 | WIPO . |
| WO89/04662 | 6/1989 | WIPO . |
| WO90/12023 | 10/1990 | WIPO . |
| WO91/01326 | 2/1991 | WIPO . |

OTHER PUBLICATIONS

M. Baba et al., "Both 2',3'-Dideoxythymidine and Its 2',3'-Unsaturated Derivative (2',3'-Dideoxythymidinene) are Potent and Selective Inhibitors of Human Immunodeficiency Virus Replication In Vitro", *Biochem. Biophys. Res. Commun.*, 142, pp. 128–134 (1987).

J. Balzarini et al., "Potent and Selective Anti–HTLV–III/LAV Activity of 2',3'-Dideoxycytidinene, the 2',3'-Unsaturated Derivative of 2',3'-Dideoxycytidine", *Biochem. Biophys. Res. Commun.*, 140, pp. 735–742 (1986).

B. Belleau et al., "Design and Activity of a Novel Class of Nucleoside Analogs Effective Against HIV–1", *V Intl. Conf. on AIDS Abs.*, T.C.O.1, p. 515 (1989).

R. Carlisle et al., "Cellular Pharmacology of the Anti–HIV BCH–189 (2'-Deoxy-3'-thiacytidine) in Human Peripheral Blood Mononuclear Cells (PBMC)" *Am. Assoc. Cancer Res. Abs. (81st Annu. Mtg.)*, 2435, p. 410 (1990).

G. Gosselin et al., "Systematic Synthesis and Biological Evaluation of α– and β–D–Lyxofuranosyl Nucleosides of the Five Naturally Occurring Nucleic Acid Bases", *J. Med. Chem.*, 30, pp. 982–991 (1987).

P. Herdewijn et al., "3'-Substituted 2',3'-Dideoxynucleoside Analogues as Potential Anti–HIV (HTLV–III/LAV) Agents", *J. Med. Chem.*, 30, pp. 1270–1278 (1987).

D. Huryn et al. "Synthesis of Iso–ddA, Member of a Novel Class of Anti–HIV Agents", *Tetrahedron Lett.*, 30, pp. 6259–6262 (1989).

D. Huryn et al. "Synthesis of Iso–ddA, Member of a Novel Class of Anti–HIV Agents: Dioxolane–T, A New 2',3'-Dideoxynucleoside Prototype with In Vitro Activity against HIV", *Chemtracts—Org. Chem.*, 3, pp. 249–251 (B. Ganem ed., 1990).

T. Lin et al., "Synthesis and Antiviral Activity of Various 3'-Azido, 3'-Amino, 2',3'-Unsaturated, and 2',3'-Dideoxy Analogues of Pyrimidine Deoxyribonucleosides against Retroviruses", *J. Med. Chem.*, 30, pp. 440–444 (1987).

(List continued on next page.)

*Primary Examiner*—Cecilia Tsang
*Attorney, Agent, or Firm*—Fish & Neave; Leslie A. McDonell; Gerald J. Flattmann, Jr.

[57] ABSTRACT

This invention relates to novel substituted 1,3-oxathiolanes and substituted 1,3-dithiolanes or pharmaceutically acceptable salts and esters thereof, of the formula:

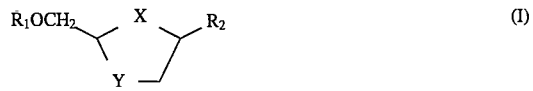

wherein
  X is S, S=O, or $SO_2$;
  Y is O, S, S=O, or $SO_2$;
  $R_1$ is hydrogen, trisubstituted silyl, $C_{1-6}$ alkyl, aralkyl, or $C_{1-6}$ acyl, and $R_2$ is a pyrimidine base or an analogue or derivative thereof.

This invention also relates to processes for preparing these compounds, intermediates useful in their preparation, to pharmaceutical compositions containing them and to the use of these compounds as antiviral agents.

18 Claims, No Drawings

OTHER PUBLICATIONS

H. Mitsuya et al., "3'-Azido-3'-deoxythymidine (BW 4509U): An Antiviral Agent that Inhibits the Infectivity and Cytopathic Effect of Human T–Lymphotropic Virus Type III/Lymphadenopathy–Associated Virus In Vitro", *Proc. Natl. Acad. Sci. USA*, 82, pp. 7096–7100 (1985).

H. Mitsuya & S. Broder, "Inhibition of the In Vitro Infectivity and Cytopathic Effect of Human T–Lymphotrophic Virus Type III/Lymphadenopathy–Associated Virus (HTLV–III/LAV) by 2',3'–Dideoxynucleosides", *Proc. Natl. Acad. Sci. USA*, 83, pp. 1911–1915 (1986).

D. Norbeck et al., "(±)–Dioxolane–T ((±)–1–[(2β, 4β)–2–(hydroxymethyl)–4–dioxolanyl]thymine)", *Tetrahedron Lett.*, 30, pp. 6263–6266 (1989).

M. Wainberg et al., "Anti–HIV–1 Activity, Toxicity and Pharmacokinetics of Totally Novel Nucleoside Analogs", *V Intl. Conf. on AIDS Abs.*, M.C.P. 63, p. 552 (1989).

M. Wainberg et al., "Characterization of AZT–Resistant Isolates of HIV–1: Susceptibility to Deoxythiacytidine and Other Nucleosides", *6th Intl. Conf. on AIDS Abs.*, 3, S.B.87, p. 117 (1990).

A. Cassinelli et al., "β–Haloalkylamine Derivatives with 1,3–Oxathiolane or 1,3–Dioxolane Nuclei", *Eur. J. Med. Chem.*,, 22, pp. 5–10 (1987).

M. Romanelli et al., "Enantioselectivity of Muscarinic Antagonists. 2,2–Dicyclohexyl–5–[(dimethylamino)methyl]–1,3–oxathiolane Methiodides and Related 3–Oxides", *J. Med. Chem.*, 31, pp. 1698–1702 (1988).

E. Teodori et al., "Resolution, Absolute Configuration, and Cholinergic Enantioselectivity of (−)–and (+)–c–2–Methyl–r–5–[(dimethylamino)methyl]–1,3–oxathiolane t–3–Oxide Methiodide and Related Sulfones", *J. Med. Chem.*, 30, pp. 1934–1938 (1987).

B. Belleau et al., "A Novel Class of 1,3–Oxathiolane Nucleoside Analogues Having Potent Anti–HIV Activity", *Bioorg. Med. Chem. Lett.*, 3(8), pp. 1723–1728 (1993).

B. Belleau et al., "A Novel Class of 1,3 Oxathiolane Nucleoside Analogues Having Potent Anti–HIV Activity, " *Chem. Abstr.*, 120:192195h (1993).

Wang et al., "Synthesis of Optically Active 2',2'–Dideoxy–3'–oxa–4'–thio–ribonucleoside Analogues by Transposition of a Leaving Group on Chiral Oxathiolanes via a Reductive–oxidative Process", *Tetrahedron Lett.*, 35(27), pp. 4739–4742 (1994).

Mansour et al., "Anti–Human Immunodeficiency Virus and Anti–Hepatitis–B Virus Activities and Toxicities of the Enantiomers of 2'–Deoxy–3'–oxa–4'–thiocytidine and Their 5–Fluoro Analogues In Vitro," *J. Med. Chem.*, 38(1), pp. 1–4 (1995).

Saari et al. J. Med. Chem. 1992, 35, 3792–3802.

Saunders, Drug Design and Discovery; 1992, vol. 8, pp. 255–263.

Connolly et al, Antimicrobial Agents and Chemotherapy, Feb. 1992, pp. 245–254.

SUBSTITUTED 1,3-OXATHIOLANES AND SUBSTITUTED 1,3-DITHIOLANES WITH ANTIVIRAL PROPERTIES

This application is a continuation-in-part of application Ser. No. 07/791,441 filed on Nov. 13, 1991, abandoned, which is a continuation-in-part of application Ser. No. 07/612,840 filed Nov. 13, 1990, now abandoned.

The present invention relates to novel substituted 1,3-oxathiolane and substituted 1,3-dithiolane compounds having pharmacological activity, to intermediates useful in their preparation, to pharmaceutical compositions containing them, and to the use of these compounds in the antiviral treatment of mammals.

Retroviral infections are a serious cause of disease, most notably, the acquired immunodeficiency syndrome (AIDS). The human immunodeficiency virus (HIV) has been recognized as the etiologic agent of AIDS. Compounds having an inhibitory effect on HIV multiplication or otherwise effective in the therapy of retroviral infections are being actively sought.

H. Mitsuya et al., "3'-Azido-3'-deoxythymidine (BW A509U): An antiviral agent that inhibits the infectivity and cytopathic effect of human T-lymphotropic virus type III/lymphadenopathy-associated virus in vitro", *Proc. Natl. Acad. Sci. U.S.A.*, 82, pp. 7096–7100 (1985), refers to 3'-azido-3'-deoxythymidine of formula (A), commonly referred to as AZT. This compound is said to be useful in providing some protection for AIDS carriers against the cytopathogenic effect of immunodeficiency virus (HIV).

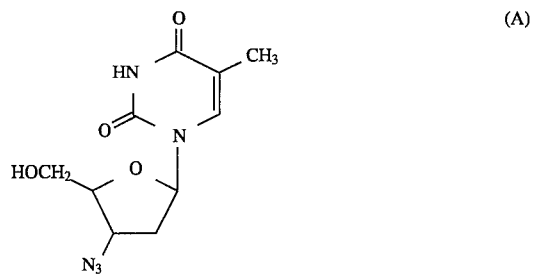
(A)

H. Mitsuya and S. Broder, "Inhibition of the in vitro infectivity and cytopathic effect of human T-lymphotrophic virus type III/lymphadenopathy-associated virus (HTLV-III/LAV) by 2',3'-dideoxynucleosides", *Proc. Natl. Aced. Sci. U.S.A.*, 83, pp. 1911–15 (1986), have also referred to a group of 2',3'-dideoxynucleosides shown in formula (B) which are said to possess protective activity against HIV-induced cytopathogenicity.

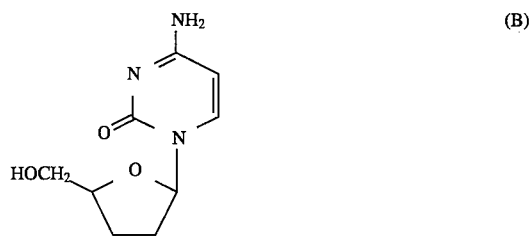
(B)

P. Herdewijn et el., "3'-Substituted 2',3'-dideoxynucleoside analogues as potential anti-HIV(HTLV-III/LAV) agents", *J. Med. Chem.*, 30, pp. 1270–1278 (1987), describe the anti-HIV activity of a series of 3'-substituted nucleoside analogues. While 3'-fluoro analogues of 3'-deoxythymidine and 2',3'-dideoxy-cytidine shown in formulas (C) and (D) are found to possess potent antiretroviral activity, substituents linked to the 3'-carbon via a thio or oxygen bridge did not yield active products.

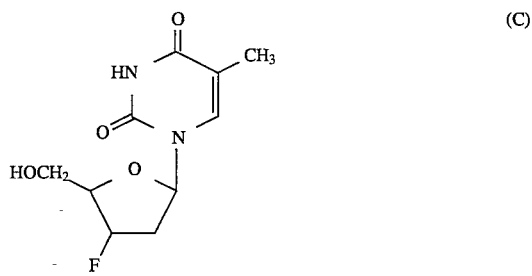
(C)

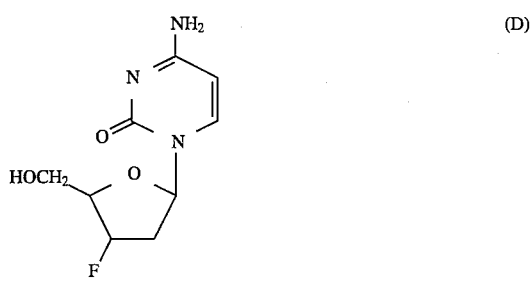
(D)

Analysis of molecular conformation studies in P. Van Roey et al., "Correlation between preferred sugar ring conformation and activity of nucleoside analogues against human immunodeficiency virus", *Proc. Natl. Acad. Sci. U.S.A.*, 86(10), pp. 3929–3933 (1989), indicate that active anti-HIV nucleoside analogues have 3' carbon conformations on the side opposite to the base.

D. Huryn et al., "Synthesis of iso-ddA, member of a novel class of anti-HIV agents", *Tetrahedron Lett.*, 30(46), pp. 6259–6262 (1989), refer to the iso-nucleoside analogue of formula (E) as a stable inhibitor of HIV replication.

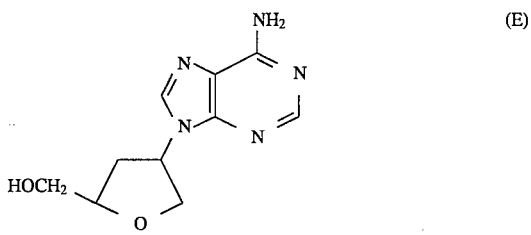
(E)

R. Vince and M. Hua, "Synthesis and anti-HIV activity of carbocyclic 2',3'-didehydro-2',3'-dideoxy 2,6-disubstituted purine nucleosides", *J. Med. Chem.*, 33 (1), pp. 17–21 (1990), describe the analogies shown in formulas (F) and (G) as having anti-HIV activity. The unsaturated analogue (F) shows greater selectivity and potency as an inhibitor of HIV replication than the saturated analog (G).

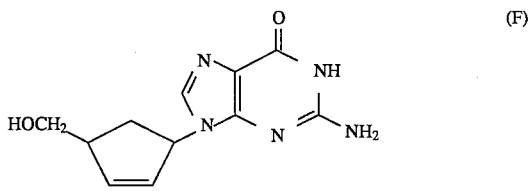
(F)

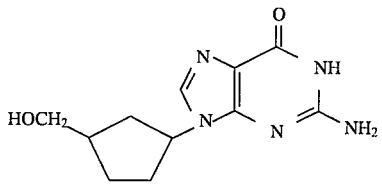

C. Chu et al., "Synthesis and structure-activity relationships of 6-substituted 2',3'-dideoxypurine nucleosides as potential anti-human immunodeficiency virus agents", *J. Med. Chem.*, 33(6), pp. 1553–1561 (1990), describe the $N_6$-methyl derivative shown in formula (H) as having greater potency against HIV than unmethylated 2',3'-dideoxyadenosine.

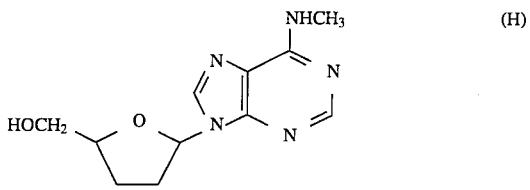

Finally, B. Belleau et al., "Design and activity of a novel class of nucleoside analogues effective against HIV-1", Abstracts of papers, Fifth International Conference on AIDS, Montreal, T.C.O. 1, p. 515 (1989), refer to dioxolanes and oxathiolanes of formulas (J) and (K) as having potent anti-HIV activity.

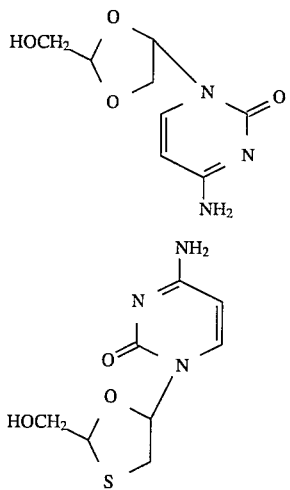

Despite these developments to date, and in view of the increasing incidence and life threatening characteristics of AIDS, there is a great need for the discovery and development of new potent and non-toxic inhibitors of HIV.

Two structurally distinct classes of compounds known as 2-substituted 4-substituted 1,3-oxathiolanes and 2-substituted 4-substituted 1,3-dithiolanes have been found to have potent antiviral activity. In particular, these compounds have been found to act as potent inhibitors of HIV-1 replication in T-lymphocytes over a prolonged period of time with less cytotoxic side effects than compounds known in the art. These compounds are also useful in prophylaxis and treatment of hepatitis B virus infections.

There are accordingly provided in a first aspect of this invention compounds of formula (I)

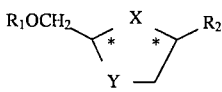

wherein

X is S, S=O, or $SO_2$;

Y is O, S, S=O, or $SO_2$;

$R_1$ is hydrogen; and $R_2$ is a pyrimidine base or an analogue or derivative thereof; and pharmaceutically acceptable salts and esters thereof.

It will be appreciated by those skilled in the art that the compounds of formula (I) contain at least two chiral centers (shown as * in formula (I)) and thus exist in the form of two pairs of optical isomers (i.e., enantiomers) and mixtures thereof including racemic mixtures. Thus the compounds of formula (I) may be either cis isomers, as represented by formula (II), or trans isomers, as represented by formula (III), or mixtures thereof. Each of the cis and trans isomers can exist as one of two enantiomers or as mixtures thereof including racemic mixtures. All such isomers and mixtures thereof including racemic mixtures are included within the scope of the invention.

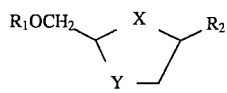

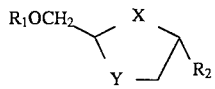

The compounds of formula (I) are preferably in the form of their cis isomers.

It will also be appreciated that when X is S=O and Y is O, S, or $SO_2$, the compounds exist in two additional isomeric forms as shown in formulas (IIa) and (IIb). These isomers differ in the configuration of the oxide oxygen atom relative to the 2,4-substituents.

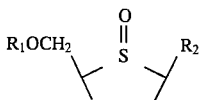

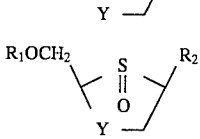

It will be further appreciated that when X is S=O and Y is S=O the compounds exist in four additional isomeric forms as shown in formulas (IIc)–(IIf). These isomers differ in the configuration of the oxide oxygen atom relative to the 2,4-substituents. Similar isomeric forms exist for the trans compounds of formula (III).

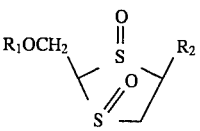

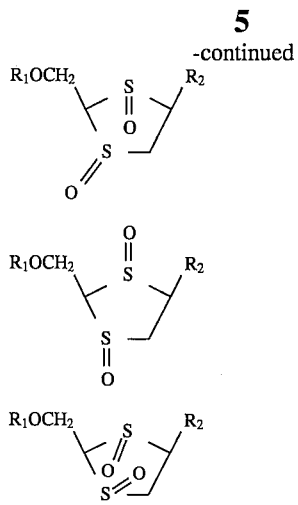

(IId)

(IIe)

(IIf)

The compounds of the invention additionally embrace such isomers and mixtures thereof.

The $R_2$ pyrimidine base or analogue or derivative thereof, depicted in formula (I), will be preferably linked at the 1-position. By pyrimidine base or analogue or derivative thereof is meant a pyrimidine base found in native nucleosides or an analogue thereof which mimics such bases in that their structures (the kinds of atoms and their arrangement) are similar to the native bases but may either possess additional or lack certain of the functional properties of the native bases. Such analogues include those derived by replacement of a CH moiety by a nitrogen atom (for example, 5-azapyrimidines such as 5-azacytosine) or vice verse. By derivatives of such bases or analogues are meant those compounds wherein ring substituents are either incorporated, removed, or modified by conventional substituents known in the art, e.g., halogen, hydroxyl, amino, $C_{1-6}$ alkyl. Such pyrimidine bases, analogues and derivatives will be well known to those skilled in the art.

Conveniently the group $R_2$ is selected from:

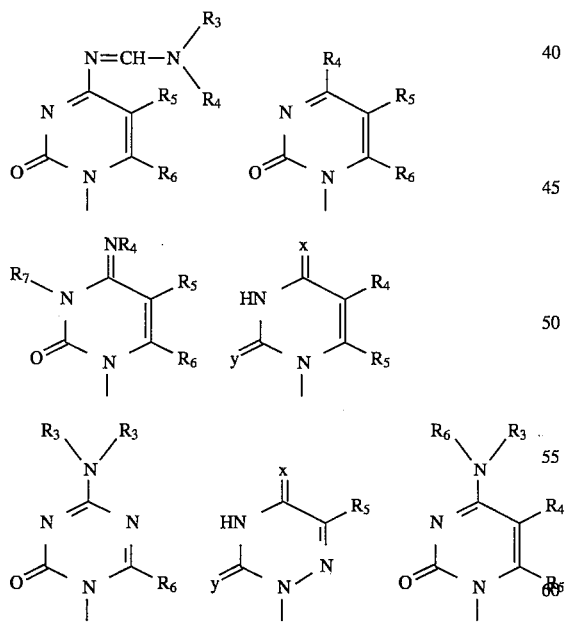

wherein:

x is O or S, y is O or S;

each $R_3$ is independently selected from the group consisting of hydrogen, $C_{1-10}$ acyl, hydroxyl, amino, $C_{1-6}$ alkyl, $C_{2-6}$ alkenyl or alkynyl, and carboxyl;

$R_4$, $R_5$ and $R_6$ are independently selected from the group consisting of hydrogen, hydroxymethyl, trifluoromethyl, $C_{1-6}$ alkyl, $C_{2-6}$ alkenyl or alkynyl, bromine, chlorine, fluorine, iodine, hydroxyl, amino, cyano, carboxyl, carbamoyl, alkoxycarbonyl, thioaryl, acyloxy, thiocarboxy, thiocarbamoyl, carbamate, ureido, amidino, aryloxy, carboxamide, and ethoxycarbonyl; and $R_7$ is selected from the group consisting of hydrogen, bromine, chlorine, fluorine, iodine, substituted or unsubstituted amino, hydroxyl, $C_{1-10}$ acyl, $C_{1-10}$ alkyl, and $C_{7-20}$ aralkyl.

A preferred $R_2$ group is:

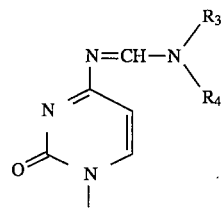

and pharmaceutically acceptable salts and esters, wherein $R_3$ is selected from the group of hydrogen, $C_{1-10}$ acyl (e.g., acetyl), hydroxyl, $C_{1-6}$ alkyl, $C_{2-6}$ alkenyl or alkynyl (e.g. propynyl); and $R_4$ is selected from the group of hydrogen, hydroxymethyl, trifluoromethyl, $C_{1-6}$ alkyl, $C_{2-6}$ alkenyl or alkynyl, bromine, chlorine, fluorine, iodine, and thioaryl.

Another preferred $R_2$ group is:

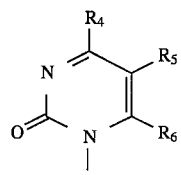

and pharmaceutically acceptable salts and esters, wherein $R_4$ and $R_5$ are independently selected from the group of hydrogen, hydroxymethyl, trifluoromethyl, $C_{1-6}$ alkyl, $C_{2-6}$ alkenyl or alkynyl, bromine, chlorine, fluorine, iodine, and thioaryl; and $R_6$ is selected from the group of hydrogen, bromine, chlorine, fluorine, iodine, cyano, carboxy, carboxamide, ethoxycarbonyl, carbamoyl, and thiocarbamoyl.

Another preferred $R_2$ group is:

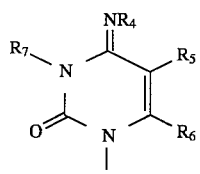

and pharmaceutically acceptable salts and esters, wherein $R_4$ to $R_6$ are as defined above; and $R_7$ is selected from the group of hydrogen, bromine, chlorine, fluorine, iodine, substituted or unsubstituted amino, and hydroxy.

A further preferred R₂ group is:

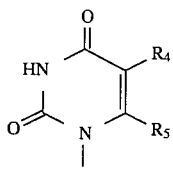

and pharmaceutically acceptable salts and esters, wherein R₄ and R₅ are as defined above.

A further preferred R₂ group is:

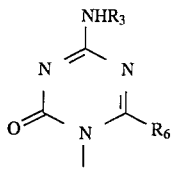

and pharmaceutically acceptable salts and esters, wherein R₃ and R₆ are as defined above.

A further preferred R₂ group is:

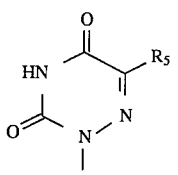

and pharmaceutically acceptable salts and esters, wherein R₅ is as defined above.

Still, a further preferred R₂ group is:

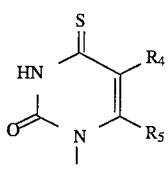

and pharmaceutically acceptable salts and esters, wherein R₄ and R₅ are as defined above.

A further preferred R₂ group is:

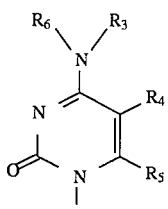

and pharmaceutically acceptable salts and esters, wherein R₃ to R₆ are as defined above.

Still, a further preferred R₂ group is:

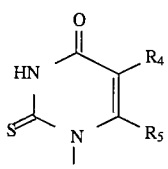

and pharmaceutically acceptable salts and esters, wherein R₄ to R₅ are as defined above.

Most preferably R₂ is:

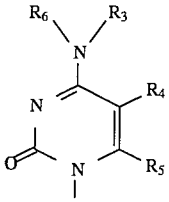

wherein $R_3$ is selected from the group of hydrogen, $C_{1-10}$ acyl (e.g., acetyl), hydroxyl, $C_{1-6}$ alkyl, $C_{2-6}$ alkenyl or alkynyl (e.g. propynyl);

$R_4$ and $R_5$ are independently selected from the group of hydrogen, hydroxymethyl, trifluoromethyl, $C_{1-6}$ alkyl, $C_{2-6}$ alkenyl or alkynyl, bromine, chlorine, fluorine, iodine, and thioaryl; and $R_6$ is selected from the group of hydrogen, bromine, chlorine, fluorine, iodine, cyano, carboxy, carboxamide, ethoxycarbonyl, carbamoyl, and thiocarbamoyl.

Preferably, Y is —O—.

Preferred 2-substituted 4-substituted 1,3oxathiolanes of this invention are compounds of formula (Ia):

wherein X is S, SO, and $SO_2$;

$R_1$ is hydrogen,; and preferably, $R_2$ is a heterocyclic radical selected from the group consisting of:

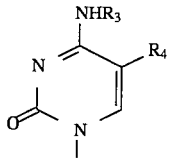

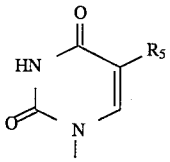

and

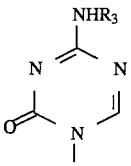

wherein $R_3$ is selected from the group of hydrogen, $C_{1-10}$ acyl (e.g., acetyl), hydroxyl, $C_{1-6}$ alkyl, $C_{2-6}$ alkenyl or alkynyl (e.g. propynyl); and $R_4$ and $R_5$ are independently selected from the group of hydrogen, hydroxymethyl, trifluoromethyl, $C_{1-6}$ alkyl, $C_{2-6}$ alkenyl or alkynyl, bromine, chlorine, fluorine, iodine, and thioaryl.

Preferred 2-substituted 4-substituted 1,3-dithiolanes of this invention are compounds of formula (Ib):

wherein each X is independently selected from the group consisting of S, S=O, and $SO_2$;

$R_1$ is hydrogen; and preferably, $R_2$ is a heterocyclic radical selected from the group consisting of:

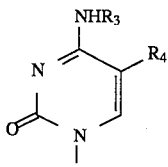

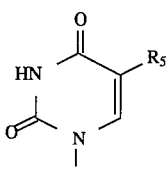

and

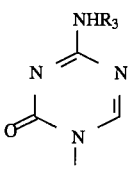

wherein $R_3$ is selected from the group of hydrogen, $C_{1-10}$ acyl (e.g., acetyl), hydroxyl, $C_{1-6}$ alkyl, $C_{2-6}$ alkenyl or alkynyl (e.g. propynyl); and $R_4$ and $R_5$ are independently selected from the group of hydrogen, hydroxymethyl, trifluoromethyl, $C_{1-6}$ alkyl, $C_{2-6}$ alkenyl or alkynyl, bromine, chlorine, fluorine, iodine, and thioaryl.

As used herein, the term "acyl" refers to a radical derived from a carboxylic acid, substituted or unsubstituted, by replacement of the —OH group. Like the acid to which it is related, an acyl radical may be aliphatic or aromatic, substituted or unsubstituted, and whatever the structure of the rest of the molecule may be, the properties of the functional group remain essentially the same. The use of the term "aroyl" is meant to refer to acyl groups derived from aromatic acids and describes a preferred subset of the term "acyl". Other suitable acyl groups will include, for example: acetyl, propionyl, isobutanoyl, pivaloyl, hexanoyl, trifluoroacetyl, chloroacetyl, cyclohexanoyl, chlorobenzoyl, methoxybenzoyl, trifluoromethylbenzoyl, 1-naphthaloyl, 2-naphthaloyl, phenacyl, nitrobenzoyl, α-hydroxy-α-phenylacetyl, α-methoxy-α-phenylacetyl, aminoacetyl, α-amino-β-phenylpropionyl, and α-methoxy-α-(trifluoromethyl) phenacyl.

As used herein, "a pharmaceutically acceptable derivative" means any pharmaceutically acceptable salt, ester, or salt of such ester, of a compound of formula (I) or any other compound which, upon administration to the recipient, is capable of providing (directly or indirectly) a compound of formula (I) or an antivirally active metabolite or residue thereof.

Pharmaceutically acceptable salts of the compounds of formula (I) include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, p-toluene sulfonic, tartaric, acetic, citric, methanesulfonic, formic, benzoic, malonic, naphthalene-2-sulfonic and benzenesulfonic acids. Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $N\text{-}(C_{1-4} \text{ alkyl})_4^+$ salts.

References hereinafter to a compound according to the invention include both compounds of formula (I) and their pharmaceutically acceptable salts and esters.

It will be appreciated by those skilled in the art that the compounds of formula (I) may be modified to provide pharmaceutically acceptable salts and esters thereof, at functional groups in both the base moiety, $R_2$, and at the hydroxymethyl group of the oxathiolane or dithiolane ring. Modification at all such functional groups is included within the scope of the invention. However, of particular interest are pharmaceutically acceptable salts and esters (e.g., esters or esters of amino acids) obtained by modification of the 2-hydroxymethyl group of the oxathiolane or dithiolane ring.

Preferred esters of the compounds of formula (I) include the compounds in which $R_1$ is replaced by a carboxyl function R—(CO) in which the non-carbonyl moiety R of the ester grouping is selected from hydrogen, straight or branched chain alkyl (e.g., methyl, ethyl, n-propyl, t-butyl, n-butyl), alkoxyalkyl (e.g., methoxymethyl), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy); substituted dihydro pyridinyl (e.g., N-methyldihydro pyridinyl); sulphonate esters such as alkyl- or aralkylsulphonyl (e.g., methanesulphonyl); sulfate esters; amino acid esters (e.g., L-valyl or L-isoleucyl) and mono, di- or triphosphate esters.

Also included within the scope of such esters are esters derived from polyfunctional acids such as carboxylic acids containing more than one carboxyl group, for example, dicarboxylic acids $HO_2C(CH_2)_nCO_2H$ where n is an integer of 1 to 10 (for example, succinic acid) or phosphoric acids. Methods for preparing such esters are well known. See, for example, E. Hahn et al., "Nucleotide dimers as anti-human immunodeficiency virus agents", *Nucleotide Analogues As Antiviral Agents*, J. C. Martin, Ed. Symposium Series #401, American Chemical Society, pp. 156–159 (1989) and M.

Busso et al., "Nucleotide dimers suppress HIV expression in vitro", *AIDS Research and Human Retroviruses,* 4(6), pp. 449–455 (1988). Where esters are derived from such acids, each acidic group is preferably esterified by a compound of formula (I) or other nucleosides or analogues and salts and esters thereof to provide esters of the formula (IV) where:

W is —O—(CO)—$(CH_2)_n$—(CO)—O— and n is an integer of 1 to 10

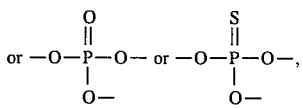

J is any nucleoside or nucleoside analogue or derivative thereof and X, Y, and $R_2$ are as defined above. Among the preferred nucleosides and nucleoside analogues are 3'-azido-3'-deoxythymidine, 2',3'-dideoxycytidine, 2',3'-dideoxyadenosine, 2',3'-dideoxyinosine, 2',3'-dideoxythymidine, 2',3'-dideoxy-2',3'-didehydrothymidine, and 2',3'-dideoxy-2',3'-didehydrocytidine and ribavirin and those nucleosides whose bases are depicted on page 8 of this specification. The preferred ester of this invention is a homodimer consisting of two nucleosides of formula (I).

With regard to the above described esters, unless otherwise specified, any alkyl moiety present advantageously contains 1 to 16 carbon atoms, preferably 1 to 4 carbon atoms and could contain one or more double bonds. Any aryl moiety present in such esters advantageously comprises a phenyl group.

In particular the esters may be a $C_{1-16}$ alkyl ester, an unsubstituted benzoyl ester or a benzoyl ester substituted by at least one halogen (bromine, chlorine, fluorine or iodine), $C_{1-6}$ alkyl or alkenyl, saturated or unsaturated $C_{1-6}$ alkoxy, nitro or trifluoromethyl groups.

Specific compounds of formula (I) include:

cis-2-hydroxymethyl-4-(cytosin-1'-yl)-1,3-oxathiolane (BCH-270), trans-2-hydroxymethyl-4-(cytosin-1'-yl)-1,3-oxathiolane, and mixtures thereof;

cis-2-hydroxymethyl-4-(uracil-1'-yl)-1,3-oxathiolane, trans-2-hydroxymethyl-4-(uracil-1'-yl)-1,3-oxathiolane, and mixtures thereof;

cis-2-hydroxymethyl-4-(thymin-1'-yl)-1,3-oxathiolane, trans-2-hydroxymethyl-4-(thymin-1'-yl)-1,3-oxathiolane, and mixtures thereof;

cis-2-hydroxymethyl-4-(5'-fluorocytosin-1'-yl)-1,3-oxathiolane (BCH-1081);

2R-hydroxymethyl-4R-(cytosin-1'-yl)-1,3-oxathiolane (BCH-1512), 2S-hydroxymethyl-4S-(cytosin-1'-yl)-1,3-oxathiolane (BCH-1533), 2R-hydroxymethyl-4S-(cytosin-1'-yl)-1,3-oxathiolane (BCH-1511), 2S-hydroxymethyl-4R-(cytosin-1'-yl)-1,3-oxathiolane (BCH-1532), and mixtures thereof 2R-hydroxymethyl-4R-(5'-fluorocytosin-1'-yl)-1,3-oxathiolane (BCH-1530), 2S-hydroxymethyl-4S-(5'-fluorocytosin-1'-yl)-1,3-oxathiolane (BCH-1529), 2R-hydroxymethyl-4S-(5'-fluorocytosin-1'-yl)-1,3-oxathiolane (BCH-1531), 2S-hydroxymethyl-4R-(5'-fluorocytosin-1'-yl)-1,3-oxathiolane (BCH-1528), and mixtures thereof cis-2-hydroxymethyl-4-(cytosin-1'-yl)-1,3-dithiolane (BCH-373), trans-2-hydroxymethyl-4-(cytosin-1'-yl)-1,3-dithiolane, and mixtures thereof;

cis-2-hydroxymethyl-4-(5'-fluorocytosin-1'-yl)-1,3-dithiolane (BCH-1026), trans-2-hydroxymethyl-4-(5'-fluorocytosin-1'-yl)-1,3-dithiolane (BCH-1040), and mixtures thereof;

and pharmaceutically acceptable salts and esters thereof in the form of a racemic mixture or single enantiomer.

Preferred compounds of formula (I) are: cis-2-hydroxymethyl-4-(cytosin-1'-yl)-1,3-oxathiolane (BCH-270); cis-2-hydroxymethyl-4-(5'-fluorocytosin-1'-yl)-1,3-oxathiolane (BCH-1081); cis-2-hydroxymethyl-4-(cytosin-1'-yl)-1,3-dithiolane (BCH-373); and cis-2-hydroxymethyl-4-(5'-fluorocytosin-1'-yl)-1,3-dithiolane (BCH-1026) and pharmaceutically acceptable salts and esters thereof in the form of racemic mixtures or single enantiomers.

Most preferred compounds of formula (I) are: 2R-hydroxymethyl-4R-(cytosin-1'-yl)-1,3-oxathiolane (BCH-1512), 2S-hydroxymethyl-4S-(cytosin-1'-yl)-1,3-oxathiolane (BCH-1533), 2R-hydroxymethyl-4R-(5'-fluorocytosin-1'-yl)-1,3-oxathiolane (BCH-1530), and 2S-hydroxymethyl-4S-(5'-fluorocytosin-1'-yl)-1,3-oxathiolane (BCH-1529).

In the processes for preparing the compounds of this invention, the following definitions are used:

$R_2$ is a pyrimidine base or an analogue or derivative thereof;

$R_w$ is hydrogen, trisubstituted silyl, $C_{1-6}$ alkyl, aralkyl such as benzyl or trityl, $C_{1-16}$ acyl, preferably a benzoyl or a benzoyl substituted in any position by at least one halogen (bromine, chlorine, fluorine or iodine), $C_{1-6}$ alkyl, $C_{1-6}$ alkoxy, nitro, or trifluoromethyl group;

$R_x$ is $C_{1-6}$ alkyl; and

L is a "leaving group", i.e., an atom or group which is displaceable upon reaction with an appropriate base, with or without a Lewis acid. Suitable leaving groups include acyloxy groups, alkoxy groups, e.g., alkoxy carbonyl groups such as ethoxy carbonyl; halogens such as iodine, bromine, chlorine, or fluorine; amido; azido; isocyanato; substituted or unsubstituted, saturated or unsaturated thiolates, such as thiomethyl or thiophenyl; substituted or unsubstituted, saturated or unsaturated seleno or selenino compounds, such as phenyl selenide or alkyl selenide; and substituted or unsubstituted, saturated or unsaturated aliphatic or aromatic ketones such as methyl ketone.

A suitable leaving group may also be —OR, where R is a substituted or unsubstituted, saturated or unsaturated alkyl group, e.g., $C_{1-6}$ alkyl or alkenyl group; a substituted or unsubstituted aliphatic or aromatic acyl group, e.g., a $C_{1-6}$ aliphatic acyl group such as acetyl and an aromatic acyl group such as benzoyl; a substituted or unsubstituted, saturated or unsaturated alkoxy or aryloxy carbonyl group, such as methyl carbonate and phenyl carbonate; substituted or unsubstituted sulphonyl imidazolide; substituted or unsubstituted aliphatic or aromatic amino carbonyl group, such as phenyl carbamate; substituted or unsubstituted alkyl imidate group such as trichloroacetamidate; substituted or unsubstituted, saturated or unsaturated phosphonates, such as diethylphosphonate; substituted or unsubstituted aliphatic or aromatic sulphonyl group, such as tosylate; or hydrogen.

Oxathiolane compounds of formula (Ia),

wherein X is S, S=O, or $SO_2$, and their pharmaceutically acceptable salts and esters, may be prepared according to the processes discussed herein or by any method known in the art for the preparation of compounds of analogous structure.

In one such process for producing oxathiolanes of this invention, a compound of formula (V),

wherein $R_w$ is hydrogen or a hydroxyl protecting group and L is a displaceable atom or group, i.e., a leaving group, is reacted with an appropriate base.

In a second process for producing oxathiolanes of this invention, a compound of formula (VI)

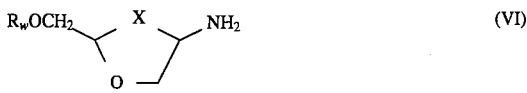

may be converted to a compound of formula (Ia) by conversion of the anomeric $NH_2$ group to the required base by methods well known in the art of nucleoside chemistry.

The 1,3-oxathiolanes of formula (Ia) may also be prepared, for example, by reaction of an aldehyde of formula (VII)

with 2-mercaptoethanol in a compatible organic solvent followed by Pummerer rearrangements as is known in the art (T. Durst, "Dimethylsulfoxide in Organic Synthesis", *Adv. Org. Chem.*, E. C. Taylor and B. Wynberg, Eds., 6, pp. 356–365 (1969)) to give 1,3-oxathiolanes of formula (V), which are converted to 1,3-oxathiolanes of formula (Ia) by methods known in the art of nucleoside chemistry.

Another process for preparing the 1,3-oxathiolanes of formula (Ia) is illustrated in SCHEME 1. Although this process is illustrated using specific reagents and compounds, it will be appreciated by one of skill in the art that suitable analogous reactants may be used to prepare analogous products, as depicted, for example, in SCHEME 1A.

SCHEME 1

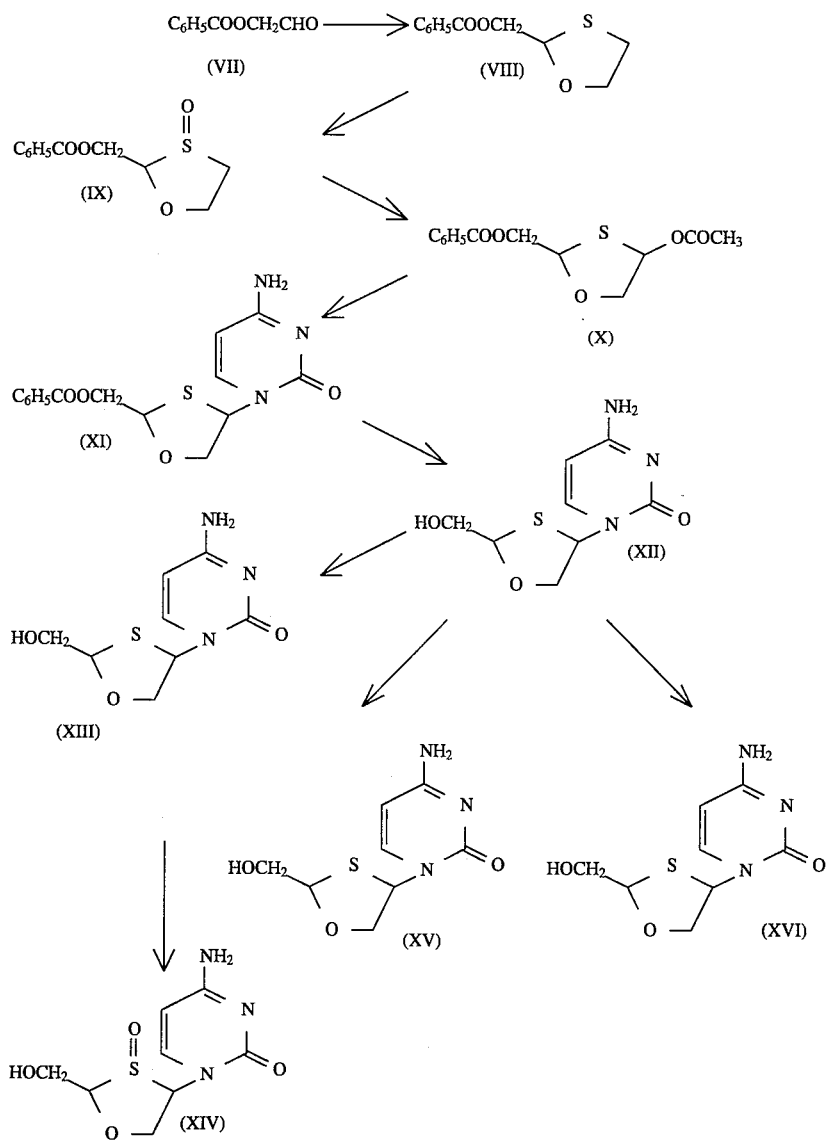

SCHEME 1A

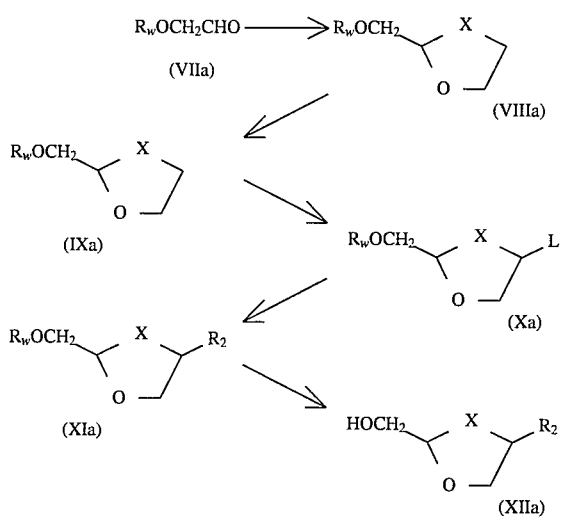

The various steps involved in the synthesis of 1,3-oxathiolanes of formula (Ia) as illustrated in SCHEME 1 may be briefly described as follows:

Step 1: Benzoyloxyacetaldehyde of formula (VII) or any aldehyde of the formula $R_wOCH_2CHO$ (C. D. Hurd and E. M. Filiachione, "A new approach to the syntheses of aldehyde sugars" *J. Am. Chem. Soc.* 61 pp 1156–1159 (1939)) is condensed with a mercaptoalcohol such as 2-mercaptoethanol in a compatible organic solvent, such as toluene, containing a catalytic amount of a strong acid to give the intermediate shown in formula (VIII).

Step 2: The 1,3-oxathiolane of formula (VIII) is then oxidized with a peracid such as magnesium monoperoxyphthalic acid in a compatible organic solvent such as methylene chloride containing a salt such as tetrabutyl ammonium bromide to give the sulfoxide intermediate shown in formula (IX).

Step 3: The sulfoxide intermediate shown in formula (IX) is treated with an acid anhydride such as acetic anhydride or any other anhydride of the formula $(R_xCO)_2O$ in the presence of a buffer such as tetra-n-butylammonium acetate to give the 2,4-disubstituted-1,3-oxathiolane of formula (X) (T. Durst, *Adv. Org. Chem.*, 6, pp. 356–365 (1969)).

Step 4: The 1,3-oxathiolane of formula (X) is then reacted with a pyrimidine base or analogue thereof, (e.g., cytosine) previously silylated with, for example, hexamethyldisilazane in a compatible solvent using a Lewis acid or trimethylsilyl triflate to give the intermediate of formula (XI) as cis and trans isomers. The isomers may be separated, preferably by chromatography, to give pure cis (XI) and pure trans (XI).

Step 5: The benzoate function of the compound of formula (XI) (cis or trans isomer), is hydrolyzed using a base such as methanolic ammonia to obtain the compound shown in formula (XII) as cis- or trans- isomer.

Step 6: The chloro function of product of formula (XII) is displaced by methanolic ammonia preferably under pressure to give the product shown in formula (XIII) as a cis- or trans-isomer.

Step 7: The preceding isomers of formula (XIII) are treated with an oxidizing agent, e.g., a suitable peracid, in a compatible organic solvent to give the 3-oxide (sulfoxide) of formula (XIV).

Step. 8: The chloro function of the compound of formula (XII) is displaced by ethanolic methylamine, preferably under pressure, to give the product shown in formula (XV) as a cis- or trans- isomer.

Step 9: The chloro function of the compound of formula (XII) is displaced by ethanolic dimethylamine, preferably under pressure, to give the product shown in formula (XVI) as a cis- or trans- isomer.

Dithiolane compounds of formula (Ib),

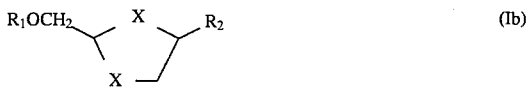

wherein each X is independently selected from S, S=O, or $SO_2$, and their pharmacologically acceptable salts and esters, may be prepared according to the processes discussed herein or by any method known in the art for the preparation of compounds of analogous structure.

In one such process for preparing the dithiolanes of this invention, a compound of formula (XVII)

wherein $R_w$ is hydrogen or hydroxyl protecting group and L is a displaceable atom or group, i.e., a leaving group, is reacted with an appropriate base.

In another process for preparing the dithiolanes of this invention, a compound of formula (XVIII)

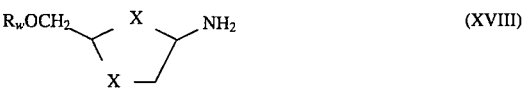

may be converted to a compound of formula (Ib) by conversion of the anomeric $NH_2$ group to the required base by methods well known in the art of nucleoside chemistry.

The 1,3-dithiolanes of formula (Ib) may also be prepared, for example, by reaction of an aldehyde of formula (VII)

$C_6H_5COOCH_2CHO$            (VII)

with 1,2-ethanedithiol in a compatible organic solvent followed by Pummerer rearrangement as is known in the art (T. Durst, *Adv. Org. Chem.*, 6, p. 356–365 (1969)) to give 1,3-dithiolanes of formula (XVII) which are converted to 1,3-dithiolanes of formula (Ib) by methods known in the art of nucleoside chemistry.

Another process for preparing the 1,3-dithiolanes of formula (Ib) is illustrated in SCHEME 2. Although this process is illustrated using specific reagents and compounds, it will be appreciated by one of skill in the art that suitable analogous reactants may be used to prepare analogous products, as depicted, for example, in SCHEME 2A.

SCHEME 2

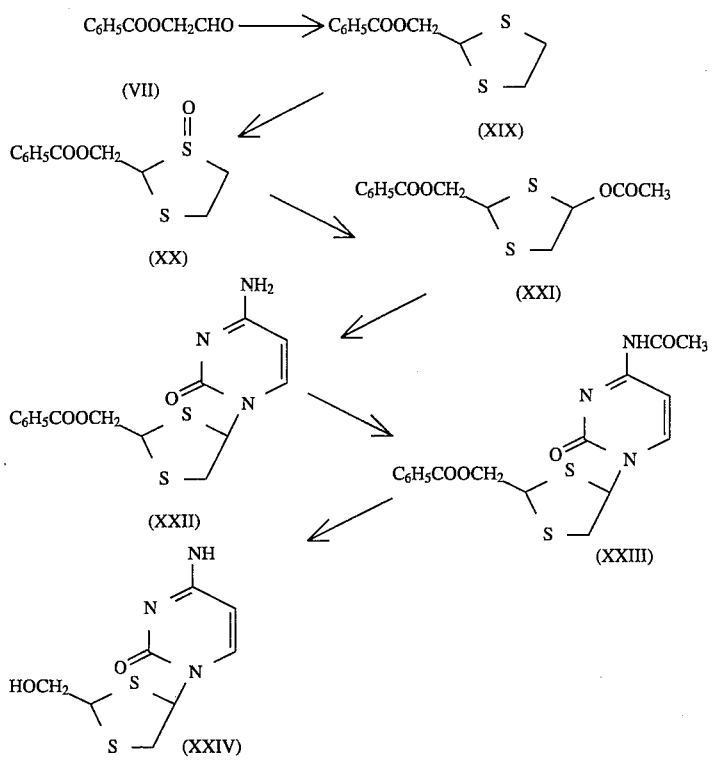

SCHEME 2A

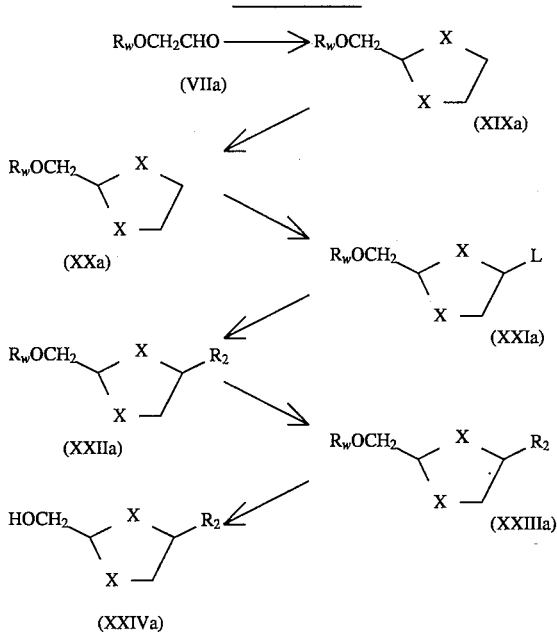

The various steps involved in the synthesis of 1,3-dithiolanes of formula (Ib) as illustrated in SCHEME 2 may be briefly described as follows:

Step 1: Benzoyloxyacetaldehyde of formula (VII) or any aldehyde of the formula $R_wOCH_2CHO$ (C. D. Hurd and E. M. Filiachione, "A new approach to the synthesis of aldehyde sugars", *J. Am. Chem. Soc.*, 61, pp. 1156–1159 (1939)) is condensed with a vicinal dithiol such as 1,2-ethanedithiol in a compatible organic solvent, such as toluene, containing a catalytic amount of a strong acid to give the intermediate shown in formula (XIX).

Step 2: The 1,3-dithiolane of formula (XIX) is then oxidized with a peracid, such as m-chloroperbenzoic acid in a compatible organic solvent, such as methylene chloride to give the sulfoxide intermediate shown in formula (XX).

Step 3: The sulfoxide intermediate shown in formula (XX) is treated with an acid anhydride, such as acetic anhydride or any other anhydride of the formula $(R_xCO)_2O$, in the presence of a base, such as sodium acetate, to give the 2,4-disubstituted-1,3-dithiolane of formula (XXI) (T. Durst, *Adv. Org. Chem.*, 6, pp. 356–365 (1969)).

Step 4: The 1,3-dithiolane of formula (XXI) is then reacted with a pyrimidine base or analogue thereof containing an $NH_2$ group (e.g., cytosine) previously silylated with, for example, hexamethyldisilazane, in a compatible solvent using a Lewis acid, such a tin IV tetrachloride or trimethylsilyl triflate, to give the intermediate of formula (XXII) as cis and trans isomers.

Step 5: The amine function of the compound shown in formula (XXII) is acetylated with acetic anhydride to yield the intermediate of formula (XXIII) as cis and trans isomers which are separated, preferably by chromatography, to give pure cis (XXIII) and pure trans (XXIII).

Step 6: The cis and trans isomers of formula (XXIII) are treated with methanolic ammonia to obtain the desired product shown in formula (XXIV) as a cis or trans isomer.

Another process for preparing the compounds of formula (Ib) is illustrated in SCHEME 3. Although this process is illustrated using specific reagents and compounds, it will be appreciated by one of skill in the art that suitable analogous reactants may be used to prepare analogous products, as depicted, for example, in SCHEME 3A.

SCHEME 3

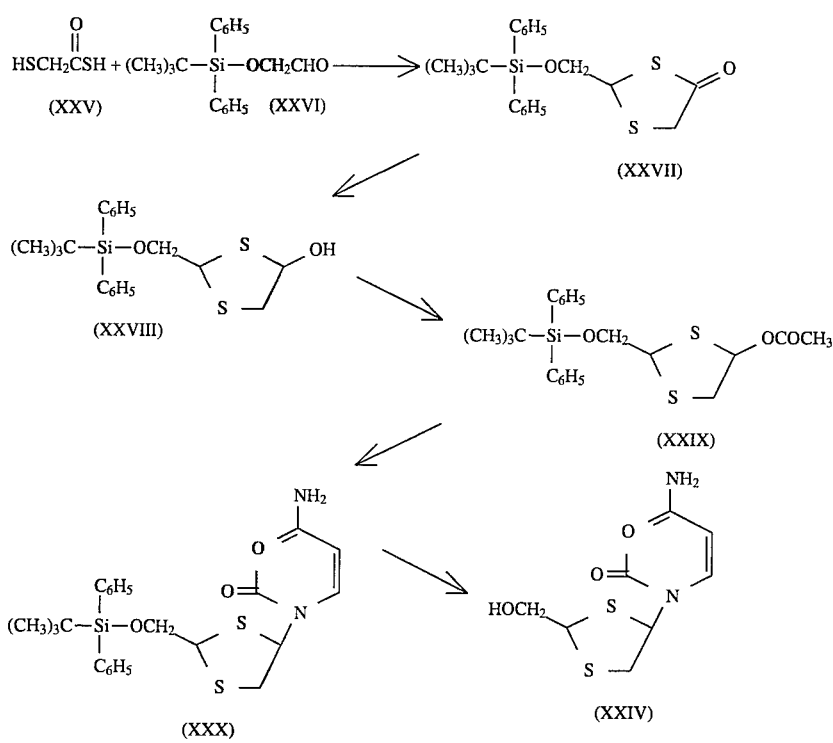

SCHEME 3A

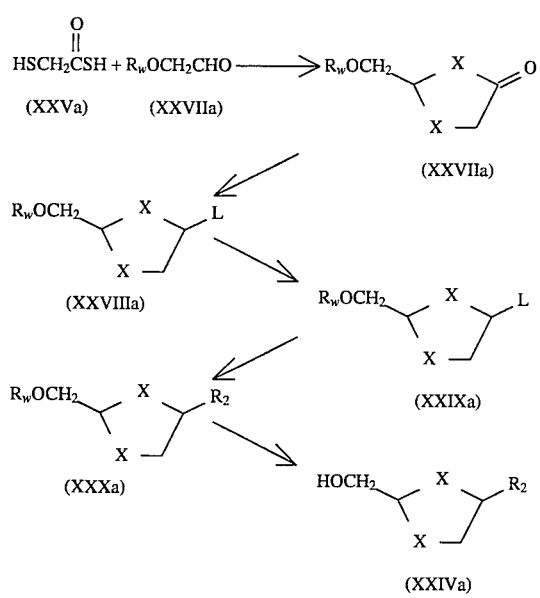

The various steps involved in the synthesis of 1,3-dithiolanes of formula (Ib) as illustrated in SCHEME 3 may be briefly described as follows:

Step 1: The known mercaptothioacetic acid of formula (XXV) (S. Satsumahyashi et al., "The Synthesis of 1,3-Dithiolanone Derivatives", *J. Org. Chem.*, 38, pp. 3953–3954 (1973) is reacted with an appropriate aldehyde of formula $R_w OCH_2 CHO$, wherein $R_w$ is preferably a silyl protecting group and more preferably, $R_w$ is a t-butyldiphenylsilyl protecting group, in a compatible solvent, in the presence of an appropriate Lewis acid such as zinc iodide to give the intermediate of formula (XXVII).

Step 2: The compound of formula (XXVII) is reduced with an appropriate reducing agent such as diisobutylaluminum hydride in a compatible organic solvent such as toluene to give the compound of formula (XXVIII).

Step 3: The compound of formula (XXVIII) is reacted with an acid anhydride or acid chloride such as acetic anhydride in the presence of pyridine and an acylation catalyst such as dimethylaminopyridine to give the compound of formula (XXIX).

Step 4: The 1,3-dithiolane of formula (XXIX) is then reacted with a pyrimidine base (e.g., cytosine) or analogue thereof previously silylated with, for example, hexamethyldisilazane in a compatible organic solvent, using a Lewis acid, such as tin IV tetrachloride to give the intermediate of formula (XXX) as cis and trans isomers.

Step 5: The cis and trans isomers of formula (XXX) are treated with tetra-n-butylammonium fluoride or other desilylating agents in an appropriate organic solvent such as tetrahydrofuran to give the desired product (XXIV) as a cis and trans isomers.

The cis and trans isomers of formula (XXIV) are separated preferably by high pressure liquid chromatography to obtain the desired 1,3-dithiolane of formula (Ib) as a pure cis or trans isomer.

Many of the reactions in the above-described processes have been extensively reported in the context of purine nucleoside synthesis, for example, in L. B. Townsend, "Chemistry of the heterocyclic moiety of purine nucleosides and some closely related analogues", *Nucleoside Analogues—Chemistry, Biology, and Medical Applications*, R. T. Walker et al., Eds., Plenum Press, New York (1979) at pages 193–223, the text of which is incorporated by reference herein.

It will be appreciated that the reactions of the above-described processes may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g., benzyl), acyl or aryl (e.g., 2,4-dinitrophenyl); subsequent removal of the protecting group being effected when desired by hydrolysis or hydrogenolysis as appropriate using standard conditions. Hydroxyl groups may be protected using any conventional hydroxyl protecting group, for example, as described in "Protective Groups in Organic Chemistry", Ed. J. F. W. McOmie (Plenum Press, 1973) or "Protective Groups in Organic Synthesis" by Theodora W. Greene (John Wiley and Sons, 1981). Examples of suitable hydroxyl protecting groups include groups selected from alkyl (e.g., methyl, t-butyl or methoxymethyl), aralkyl (e.g., benzyl, diphenylmethyl or triphenylmethyl), heterocyclic groups such as tetrahydropyranyl, acyl, (e.g., acetyl or benzoyl) and silyl groups such as trialkylsilyl (e.g., t-butyldimethylsilyl). The hydroxyl protecting groups may be removed by conventional techniques. Thus, for example, alkyl, silyl, acyl and heterocyclic groups may be removed by solvolysis, e.g., by hydrolysis under acidic or basic conditions. Aralkyl groups such as triphenylmethyl may similarly be removed by solvolysis, e.g., by hydrolysis under acidic conditions. Aralkyl groups such as benzyl may be cleaved, for example, by treatment with $BF_3$/etherate and acetic anhydride followed by removal of acetate groups so formed at an appropriate stage in the synthesis. Silyl groups may also conveniently be removed using a source of fluoride ions such as tetra-n-butylammonium fluoride.

In the above-described processes, the compounds of formula (I) are generally obtained as a mixture of the cis and trans isomers.

These isomers may be separated, for example, by acetylation, e.g., with acetic anhydride followed by separation by physical means, e.g., chromatography on silica gel and deacetylation, e.g., with methanolic ammonia or by fractional crystallization.

Pharmaceutically acceptable salts of the compounds of the invention may be prepared as described in U.S. Pat. No. 4,383,114, the disclosure of which is incorporated by reference herein. Thus, for example, when it is desired to prepare an acid addition salt of a compound of formula (I), the product of any of the above procedures may be converted into a salt by treatment of the resulting free base with a suitable acid using conventional methods. Pharmaceutically acceptable acid addition salts may be prepared by reacting the free base with an appropriate acid optionally in the presence of a suitable solvent such as an ester (e.g., ethyl acetate) or an alcohol (e.g., methanol, ethanol or isopropanol). Inorganic basic salts may be prepared by reacting the free base with a suitable base such as an alkoxide (e.g., sodium methoxide) optionally in the presence of a solvent such as an alcohol (e.g., methanol). Pharmaceutically acceptable salts may also be prepared from other salts, including other pharmaceutically acceptable salts, of the compounds of formula (I) using conventional methods.

A compound of formula (I) may be converted into a pharmaceutically acceptable phosphate or other ester by reaction with a phosphorylating agent, such as $POCl_3$, or a suitable esterifying agent, such as an acid halide or anhydride, as appropriate. An ester or salt of a compound of formula (I) may be converted to the parent compound, for example, by hydrolysis.

Where the compound of formula (I) is desired as a single isomer it may be obtained either by resolution of the final product or by stereospecific synthesis from isometrically pure starting material or any convenient intermediate.

Resolution of the final product, or an intermediate or starting material therefore may be effected by any suitable method known in the art: see for example, *Stereochemistry of Carbon Compounds*, by E. L. Eliel (McGraw Hill, 1962) and *Tables of Resolving Agents*, by S. H. Wilen.

The intermediates of formulas (Ic) and (Id) are useful in the above-described processes for making the oxathiolane and dithiolane compounds of this invention

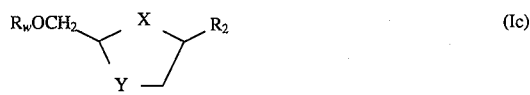

(Ic)

(Id)

wherein $R_w$ is trisubstituted silyl, $C_{1-6}$ alkyl, aralkyl such as benzyl or trityl, $C_{1-16}$ acyl, preferably a benzoyl or a benzoyl substituted in any position by at least one halogen (bromine, chlorine, fluorine or iodine), $C_{1-6}$ alkyl, $C_{1-6}$ alkoxy, nitro, or trifluoromethyl group; and $R_2$ is a pyrimidine base or an analogue or derivative thereof; and L is a leaving group as previously defined.

The following intermediates of formula (Ic) are of particular importance:

cis-2-benzoyloxymethyl-4-(cytosin-1'-yl)-1,3-oxathiolane, trans-2-benzoyloxymethyl-4-(cytosin-1'-yl)-1,3-oxathiolane, and mixtures thereof;

cis-2-benzoyloxymethyl-4-(N4'-acetylcytosin-1'-yl)-1,3-oxathiolane, trans-2-benzoyloxymethyl-4-(N4'-acetylcytosin-1'-yl)-1,3-oxathiolane, and mixtures thereof;

cis-2-benzoyloxymethyl-4-(uracil-1'-yl)-1,3-oxathiolane, trans-2-benzoyloxymethyl-4-(uracil-1'-yl)-1,3-oxathiolane, and mixtures thereof;

cis-2-benzoyloxymethyl-4-(thymin-1'-yl)-1,3-oxathiolane, trans-2-benzoyloxymethyl-4-(thymin-1'-yl)-1,3-oxathiolane, and mixtures thereof;

cis-2-benzoyloxymethyl-4-(5'-fluorocytosin-1'-yl)-1,3-oxathiolane, trans-2-benzoyloxymethyl-4-(5'-fluorocytosin-1'-yl)-1,3-oxathiolane, and mixtures thereof;

2R-t-butyldiphenylsilyloxymethyl-4S-(N4'-acetylcytosin-1'-yl)-1,3-oxathiolane, 2R-t-butyldiphenylsilyloxymethyl-4R-(N4'-acetylcytosin-1'-yl)-1,3-oxathiolane, 2S-t-butyldiphenylsilyloxymethyl-4R-(N4'-acetylcytosin-1'-yl)-1,3-oxathiolane, 2S-t-butyldiphenylsilyloxymethyl-4S-(N4'-acetylcytosin-1'-yl)-1,3-oxathiolane, and mixtures thereof;

2R-t-butyldiphenylsilyloxymethyl-4S-(N4'-acetyl-5'-fluorocytosin-1'-yl)-1,3-oxathiolane, 2R-t-butyldiphenylsilyloxymethyl-4R-(N4'-acetyl-5'-fluorocytosin-1'-yl)-1,3-oxathiolane, 2S-t-butyldiphenylsilyloxymethyl-4R-(N4'-acetyl-5'-fluorocytosin-1'-yl)-1,3-oxathiolane, 2S-t-butyldiphenylsilyloxymethyl-4S-(N4'-acetyl-5'-fluorocytosin-1'-yl)-1,3-oxathiolane, and mixtures thereof;

cis-2-benzoyloxymethyl-4-(cytosin-1'-yl)-1,3-dithiolane, trans-2-benzoyloxymethyl-4-(cytosin-1'-yl)-1,3-dithiolane, and mixtures thereof;

cis-2-benzoyloxymethyl-4-(N4'-acetylcytosin-1'-yl)-1,3-dithiolane, trans-2-benzoyloxymethyl-4-(N4'-acetylcytosin-1'-yl)-1,3-dithiolane, and mixtures thereof;

cis-2-p-nitrobenzoyloxymethyl-4-(5'-fluorocytosin-1'-yl)-1,3-dithiolane, trans-2-p-nitrobenzoyloxymethyl-4-(5'-fluorocytosin-1'-yl)-1,3-dithiolane, and mixtures thereof.

The following intermediates of formula (Id) are of particular importance:

2-benzoyloxymethyl-1,3-oxathiolane;

cis-2-benzoyloxymethyl-1-oxo-1,3-oxathiolane, trans-2-benzoyloxymethyl-1-oxo-1,3-oxathiolane, and mixtures thereof;

cis-2-benzoyloxymethyl-4-benzoyloxy-1,3-oxathiolane, trans-2-benzoyloxymethyl-4-benzoyloxy-1,3-oxathiolane, and mixtures thereof;

cis-2-benzoyloxymethyl-4-acetoxy-1,3-oxathiolane, trans-2-benzoyloxymethyl-4-acetoxy-1,3-oxathiolane, and mixtures thereof;

(1'R,2'S,5'R)-menthyl-1,3-oxathiolan-2S-carboxylate;
(1'R,2'S,5'R)-menthyl-1,3-oxathiolan-2R-carboxylate;
2R-hydroxymethyl-1,3-oxathiolane;
2S-hydroxymethyl-1,3-oxathiolane;
2S-t-butyldiphenylsilyloxymethyl-1,3-oxathiolane;
2R-t-butyldiphenylsilyloxymethyl-1,3-oxathiolane;
2R-t-butyldiphenylsilyloxymethyl-4R-acetoxy-1,3-oxathiolane, 2R-t-butyldiphenylsilyloxymethyl-4S-acetoxy-1,3-oxathiolane, and mixtures thereof;

2S-t-butyldiphenylsilyloxymethyl-4R-acetoxy-1,3-oxathiolane, 2S-t-butyldiphenylsilyloxymethyl-4S-acetoxy-1,3-oxathiolane, and mixtures thereof;

2-benzoyloxymethyl-1,3-dithiolane;

cis-2-p-nitrobenzoyloxymethyl-4-p-nitrobenzoyloxy-1,3-dithiolane, trans-2-p-nitrobenzoyloxymethyl-4-p-nitrobenzoyloxy-1,3-dithiolane, and mixtures thereof;

cis-2-benzoyloxymethyl-3-oxo-1,3-dithiolane, trans-2-benzoyloxymethyl-3-oxo-1,3-dithiolane, and mixtures thereof;

cis-2-benzoyloxymethyl-4-acetoxy-1,3-dithiolane, trans-2-benzoyloxymethyl-4-acetoxy-1,3-dithiolane, and mixtures thereof.

The compounds of the invention either themselves possess antiviral activity and/or are metabolizable into compounds possessing anti-vital activity. In particular these compounds are effective in inhibiting the replication of hepatitis B virus and retroviruses, including human retroviruses such as human immunodeficiency viruses (HIV's), the causative agents of AIDS.

There is thus provided as a further aspect of the invention a compound of formula (I) or a pharmaceutically acceptable derivative thereof for use as an active therapeutic agent in particular as an antiviral agent, for example in the treatment of hepatitis B viral and retroviral infections.

In a further or alternative aspect there is provided a method for the treatment of a viral infection, in particular an infection caused by hepatitis B virus or a retrovirus such as HIV, in a mammal, including man, comprising administration of an effective amount of an antiviral compound of formula (I) or a pharmaceutically acceptable derivative thereof.

There is also provided in a further or alternative aspect of this invention, use of a compound of formula (I) or a pharmaceutically acceptable derivative thereof for the manufacture of a medicament for the treatment of a viral infection.

The compounds of the invention are also useful in the treatment of AIDS-related conditions such as AIDS-related complex (ARC), persistent generalized lymphadenopathy (PGL), AIDS-related neurological conditions (such as dementia), anti-HIV antibody-positive and HIV-positive conditions, Kaposi's sarcoma, thrombocytopenia purpura and opportunistic infections.

The compounds of the invention are also useful in the prevention or progression to clinical illness of individuals who are anti-HIV antibody or HIV-antigen positive and in prophylaxis following exposure to HIV.

The compounds of formula (I) or the pharmaceutically acceptable salts and esters thereof, may also be used for the prevention of viral contamination of biological fluids such as blood or semen in vitro.

Certain of the compounds of formula (I) are also useful as intermediates in the preparation of other compounds of the invention.

It will be appreciated by those skilled in the art that references herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general, however, a suitable dose will be in the range from about 1 to about 750 mg/kg of body weight per day, such as 3 to about 120 mg per kilogram body weight of the recipient per day, preferably in the range of 6 to 90 mg/kg/day, most preferably in the range of 15 to 60 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to 75 μM, preferably about 2 to 50 μM, most preferably about 3 to about 30 μM. This may be achieved, for example, by the intravenous injection of a 0.1 to 5% solution of the active ingredient, optionally in saline, or administered as a bolus containing about 0.1 to about 110 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable derivative thereof together with one or more pharmaceutically acceptable carriers thereof and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

The compounds according to the invention may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored based, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutically formulations suitable for rectal administration wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the compounds of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions according to the invention may also contain other active ingredients such as antimicrobial agents, or preservatives.

The compounds of the invention may also be used in combination with other therapeutic agents, for example, other anti-infective agents. In particular the compounds of the invention may be employed together with known antiviral agents.

The invention thus provides, in a further aspect, a combination comprising a compound of formula (I) or a physiologically acceptable derivative thereof together with another therapeutically active agent, in particular, an antiviral agent.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention.

Suitable therapeutic agents for use in such combinations include acyclic nucleosides such as acyclovir, ganciclovir, interferons such as alpha-, beta- and gamma-interferon; glucuronation inhibitors such as probenecid; nucleoside transport inhibitors such as dipyridamole; nucleoside analogues such as 3'-azido-3'-deoxythymidine, 2',3'-dideoxycytidine, 2',3'-dideoxyadenosine, 2',3'-dideoxyinosine, 3'-deoxythymidine, 2',3'-dideoxy-2',3'-didehydro-thymidine, and 2',3'-dideoxy-2',3'-didehydrocytidine and ribavirin; immunomodulators such as interleukin II (IL2) and granulocyte macrophage colony stimulating factor (GM-CSF), erythropoietin, ampligen, thymomodulin, thymopentin, foscarnet, glycosylation inhibitors such as 2-deoxy-D-glucose, castanospermine, 1-deoxynojirimycin; and inhibitors of HIV binding to CD4 receptors such as soluble CD4, CD4 fragments, CD4-hybrid molecules and inhibitors of the HIV aspartyl protease such as L-735,524.

The individual components of such combinations may be administered either sequentially or simultaneously in separate or combined pharmaceutical formulations.

When the compound of formula (I) or a pharmaceutically acceptable derivative thereof is used in combination with a second therapeutic agent active against the same virus, the dose of each compound may be either the same or differ from that when the compound is used alone. Appropriate doses will be readily appreciated by those skilled in the art.

The invention will be further described by the following examples which are not intended to limit the invention in any way. All temperatures are in degrees celsius.

EXAMPLES

Example 1

BENZOYLOXYACETALDEHYDE

$C_6H_5COOCH_2CHO$ (VII)

This known intermediate was prepared by portionwise addition of $NaIO_4$ (80 g) to a mixture of 1-benzoyl glycerol (50 g), $CH_2Cl_2$ (500 ml), and $H_2O$ (25 ml) under vigorous stirring at room temperature. The resulting solution was stirred for 2 hours, $MgSO_4$ (100 g) was added and the solution stirred for an additional 30 minutes. The mixture was filtered, the filtrate evaporated in vacuo and the residue distilled in vacuo to yield 26 g of pure product.

b.p. 92°–94°/0.25 mm $^1$H NMR (200 MH$_z$; TMS as internal reference): δ (ppm in CDCl$_3$) 9.71 (s, 1H; —C$\underline{H}$O), 8.11 (d, 2H; aromatic), 7.60 (m, 1H; aromatic), 7.46 (m, 2H; aromatic), 4.88 (s, 2H; —C$\underline{H}_2$CHO).

Example 2

2-BENZOYLOXYMETHYL-1,3-OXATHIOLANE

(VIII)

A mixture of benzoyloxyacetaldehyde (example 1) (6.21 g), 2-mercaptoethanol (3 ml) and para-toluene sulfonic acid (0.2 g) in toluene (150 ml) was heated for 3 hours at refluxing under water removal conditions using a Dean Stark apparatus. The mixture was cooled to room temperature, washed first with aqueous NaHCO$_3$-solution (1×50 ml), and then with water (2.5 ml) and dried over MgSO$_4$. The solution was filtered and the filtrate evaporated under reduced pressure. The residue was purified on silica gel using hexane:ethyl acetate (9:1) as eluant. It yielded 7.63 g (90%) of pure product, which was identified by $^1$H- and $^{13}$C-NMR.

$R_f$: 0.39 (hexane:ethyl acetate)

$^1$H-NMR: δ(ppm in CDCl$_3$) 8.03 (m, 2H, aromatic), 7.53 (m, 1H, aromatic), 7.39 (m, 2H, aromatic), 5.41 (dd, 1H, C$_2$—H), 4.43 (m, 2H, C$_2$—C$_2$OCC$_6$H$_5$), 4.21 (m, 1H, C$_5$—H), 3.96 (m, 1H, C$_5$—H), 2.98 (m, 2H, C$_4$—H).

$^{13}$C-NMR: δ(ppm in CDCl$_3$) 166.82, 133.74, 130.35, 128.97, 83.58, 71.87, 66.62 and 32.74.

Example 3

2-BENZOYLOXYMETHYL-3-OXO-1,3-OXATHIOLANE

(IX)

Monoperoxyphthalic acid, magnesium salt (MMPP, 28 g) was added portionwise under vigorous stirring to a mixture of 2-benzoyloxymethyl-1,3-oxathiolane (example 2) (20 g), tetrabutyl ammonium bromide (0.4 g) in methylene chloride (200 ml), and water (200 ml). The mixture was stirred at room temperature for 30 minutes and the organic layer was collected. The aqueous phase was extracted with methylene chloride (3×75 ml) and the combined organic layer was washed first with water (2×100 ml), then with brine solution (100 ml), dried over MgSO$_4$, and filtered. The filtrate was evaporated in vacuo and the residue was purified by chromatography on silica gel using ethyl acetate as eluant to give 18.5 g (86%) of pure product as a mixture of cis- and trans-isomers in a ratio of 1:2 respectively.

m.p.: 70°–72°

$^1$H-NMR: δ(ppm in CDCl$_3$) 8.05 (m, 2H, aromatic, cis-isomer), 7.95 (m, 2H, aromatic, trans-isomer), 7.56 (m, aromatic), 7.23 (m, aromatic), 4.77 (m, 4H, C$_2$—H, C$_5$—H, and C$_2$—CH$_2$OOCC$_6$H$_5$), 4.43 (m, 1H, C$_5$—H, trans-isomer), 4.09 (m, 1H, C$_5$—H, cis-isomer), 3.11 (m, 2H, C$_4$—H, trans-isomer), 2.75 (m, 2H, C$_4$—H, cis-isomer).

$^{13}$C-NMR: δ(ppm in CDCl$_3$)

cis-isomer: 166.64, 134.02, 130.42, 129.88, 129.06, 96.16, 68.83, 59.47 and 54.30.

trans-isomer: 166.36, 134.12, 130.29, 129.68, 129.15, 108.07, 70.09, 61.83 and 53.47.

Example 4

2-BENZOYLOXYMETHYL-4-ACETOXY-1,3-OXATHIOLANE

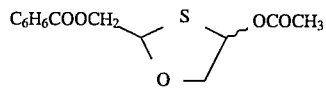
(X)

A mixture of 2-benzoyloxymethyl-3-oxo-1,3-oxathiolane (example 3) (10.5 g), tetra-n-butylammonium acetate (17 g) in acetic anhydride (250 ml) was heated at 110° to 120° C. under argon for 14 hours and cooled to room temperature. Excess acetic anhydride was removed under reduced pressure. The residue was dissolved in methylene chloride (500 ml), washed first with saturated aqueous NaHCO$_3$ (2×200 ml), then with brine solution (200 ml), dried over MgSO$_4$, filtered and evaporated in vacuo. The residue was purified by chromatography on silica gel using hexane:ethyl acetate (8:1) as eluant to give 7.4 g (60% yield) of the desired product as a mixture of cis- and trans- isomers. A small quantity of each isomer was also isolated and characterized by $^1$H- and $^{13}$C-NMR.

cis-isomer:

$R_f$: 0.43 (hexane:EtOAc)

$^1$H-NMR: δ(ppm in CDCl$_3$) 8.05 (m, 2H, aromatic), 7.58 (m, 1H, aromatic), 7.45 (m, 2H, aromatic), 6.24 (d, 1H, C$_4$—H), 5.50 (t, 1H, C$_2$—H), 4.61 (d, 1H, C$_2$—CH$_2$OOCC$_6$H$_5$), 4.53 (d, 2H, C$_5$—H), 3.94 (dd, 1H, C$_5$—H), 2.05 (s, 3H, CH$_3$).

trans-isomer:

$R_f$: 0.43 (hexane:EtOAc 7:3)

$^1$H-NMR: δ(ppm in CDCl$_3$) 8.04 (m, 2H, aromatic), 7.58 (m, 1H, aromatic), 7.45 (m, 2H, aromatic), 6.27 (dd, 1H, C$_4$—H), 5.73 (dd, 1H, C$_2$—H), 4.53 (dd, 1H, C$_2$—CH$_2$OOCC$_6$H$_5$), 4.34 (dd, 1H, C$_5$—H), 4.26 (dd, 1H, C$_2$—C$_2$OCC$_6$H$_5$), 4.20 (dd, 1H, C$_5$—H), 2.09 (s, 3H, CH$_3$).

$^{13}$C-NMR: δ(ppm in CDCl$_3$) 177.66, 166.37, 133.46, 129.93, 128.60, 83.76, 81.22, 74.33, 64.65 and 20.79.

Example 5

CIS- AND TRANS-2-BENZOYLOXYMETHYL-4-(CYTOSIN-1'-YL)-1,3-OXATHIOLANE

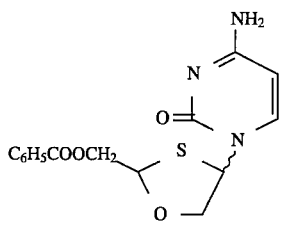 (XXXI)

A mixture of cytosine (206 mg), ammonium sulfate (10 mg) and hexamethyldisilazane (HMDS, 10 ml) was heated at refluxing under argon until a clear solution resulted. Excess reagents were evaporated in vacuo and the remaining volatile removed under high vacuum (15 minutes). The solid residue was dissolved in dry methylene chloride (20 ml) and a solution of 2-benzoyloxymethyl-4-acetoxy-1,3-oxathiolane (example 4) (350 mg) in dry methylene chloride (20 ml) was added under argon, followed by a solution of tin IV chloride ($SnCl_4$, 124 ml) in methylene chloride (20 ml) at 0° C. The reaction mixture was stirred under argon overnight at room temperature, then heated at refluxing for 3 hours and cooled to room temperature. The mixture was diluted with methylene chloride (100 ml) and poured while stirring into saturated aqueous $NaHCO_3$. The organic layer was separated by filtration over celite, washed first with water (2×75 ml), then with brine solution (100 ml), dried over $MgSO_4$ and filtered. The residue was purified by chromatography on silica gel using ethyl acetate:$CH_3OH$ as the eluant to give 140 mg (35%) of the desired product as a mixture of cis- and trans- isomers in a 1:1 ratio as determined by $^1$H-NMR. These isomers were separated as the N-acetyl derivatives in the next example.

Example 6

CIS- AND TRANS-2-BENZOYLOXYMETHYL-4-(N4'-ACETYL-CYTOSIN-1'-YL)-1,3-OXATHIOLANE

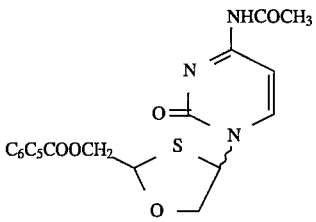 (XXXII)

A solution of the cis- and trans- mixture of 2-benzoyloxymethyl-4-(cytosin-1'-yl)-1,3-oxathiolane (example 5) (135 mg), 4-dimethylaminopyridine (DMAP, 15 mg) and acetic anhydride (44 ml) in dry pyridine (10 ml) was stirred overnight at room temperature (16 hours) and poured into cold water (100 ml) followed, by extraction with methylene chloride (3×50 ml). The extract was washed with water, dried over $MgSO_4$, filtered and evaporated in vacuo. Toluene was added to the residue, then evaporated in vacuo. Toluene was added to the residue, then evaporated in vacuo and the residual oil was purified by chromatography on silica gel using ethyl acetate as eluant to yield 65 mg of pure trans-isomer as the fast moving product and 60 mg of pure cis-isomer as the low moving product. These were characterized by $^1$H and $^{13}$C-NMR.

cis-isomer:

$^1$H-NMR: δ(ppm in $CDCl_3$) 9.61 (b, 1H, $C_4$—NH-$COCH_3$), 8.29 (d, 1H, $C_{6'}$—H), 8.06 (m, 2H, aromatic), 7.65 (m, 1H, aromatic), 7.51 (m, 2H, aromatic), 7.25 (d, 1H, $C_{5'}$—H), 6.61 (d, 1H, $C_4$—H), 5.50 (t, 1H, $C_2$—H), 4.80 (m, 2H, $C_2$—$CH_2OOCC_6H_5$), 4.48 (d, 1H, $C_5$—H), 4.05 (dd, 1H, $C_5$—H), 2.25 (s, 3H, $CH_3$).

$^{13}$C-NMR: δ(ppm in $CDCl_3$) 170.93, 166.28, 162.80, 155.76, 146.06, 133.91, 129.90, 128.84, 97.45, 85.88, 78.25, 64.60, 63.53 and 24.71.

trans-isomer:

$^1$H-NMR: δ(ppm in DMSO $d_6$) 10.88 (s, 1H, $C_4$—$NHCOCH_3$). 8.13 (d, 1H, $C_{6'}$—H), 7.96 (m, 2H, aromatic), 7.68 (m, 1H, aromatic), 7.52 (m, 2H, aromatic), 7.20 (d, 1H, $C_{5'}$—H), 6.35 (d, 1H, $C_4$—H), 5.96 (dd, 1H, $C_2$—H), 4.58 (dd, 1H, $C_2$—$CH_2OOCC_6H_5$), 4.44 (d, 1H, $C_5$—H), 4.29 (m, 2H, $C_5$—H and $CH_2OOCC_6H_5$), 2.07 (s, 3H, $CH_3$).

$^{13}$C-NMR: δ(ppm in DMSO $d_6$) 171.53, 165.84, 162.76, 155.21, 146.59, 134.00, 129.64, 129.23, 96.54, 83.78, 74.24, 64.58, 64.01 and 24.35.

Example 7

CIS- AND TRANS-2-HYDROXYMETHYL-4-(CYTOSIN-1'-YL)-1,3-OXATHIOLANE

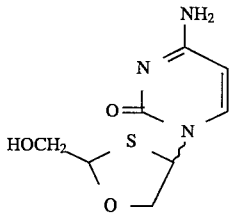 (XXXIII)

cis-isomer (BCH-270):

A solution of cis-2-benzoyloxymethyl-4(N4'-acetyl-cytosin-1'-yl)-1,3-oxathiolane (example 6) (54 mg) in methanolic ammonia (50 ml) was stirred overnight at room temperature (16 hours). The solvent was evaporated in vacuo and the residue treated with ether yielding 37 mg (90%) of desired product. The product was then characterized by $^1$H- and $^{13}$C-NMR.

m.p.: 213°–215° C.

UV: ($CH_3OH$) Lamda max: 270 nm $^1$H-NMR: δ(ppm in, DMSO $d_6$) 7.85 (d, 1H, $C_{6'}$—H), 7.16 (d, 2H, $C_{4'}$—$NH_2$), 6.34 (d, 1H, $C_{4'}$—H), 5.76 (d, 1H, $C_{5'}$—H), 5.31 (t, 1H, $C_2$—$C_2O\underline{H}$), 5.18 (t, 1H, $C_2$—H), 4.40 (d, 1H, $C_5$—H), 3.92 (dd, 1H, $C_5$—H), 3.78 (m, 2H, $C_2$—$C\underline{H}_2OH$).

$^{13}$C-NMR: δ(ppm in DMSO $d_6$) 165.95, 155.74, 142.39, 94.98, 88.85, 77.29, 62.91 and 62.48.

trans-isomer:

A solution of trans-2-benzoyloxymethyl-4-($N_{4'}$-acetyl-cytosin-1'-yl)-1,3-oxathiolane (example 6) (63 mg) in methanolic ammonia (50 ml) was stirred overnight at room temperature (16 hours). The solvent was removed in vacuo and the residue was solidified with ether to give 36 mg (93%) of the desired product which was characterized by $^1$H- and $^{13}$C-NMR.

m.p.: 175°–177° C.

UV: ($CH_3OH$) Lamda max: 270 nm.

$^1$H-NMR: δ(ppm in DMSO d$_6$) 7.67 (d, 1H, C$_6$·—H), 7.19 (d, 2H, C$_4$·—NH$_2$), 6.30 (d, 1H, C$_4$—H), 5.77 (d, 1H, C$_5$·—H), 5.56 (t, 1H, C$_2$—C$_2$OH), 5.23 (t, 1H, C$_2$—H), 4.18 (m, 2H, C$_5$—H), 3.61 (m, 1H, C$_2$—CH$_2$OH), 3.36 (m, 1H, C$_2$—C$_2$OH).

$^{13}$C-NMR: δ(ppm in DMSO d$_6$) 166.00, 155.65, 142.30, 95.11, 87.52, 74.52, 63.42 and 62.86.

Example 8

CIS- AND TRANS-2-BENZOYLOXYMETHYL-4(URACIL-1'-YL)-1,3-OXATHIOLANE

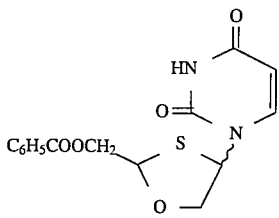

(XXXIV)

A mixture of uracil (446 mg), ammonium sulfate (20 mg) and hexamethyldisilazane (HMDS, 15 ml) was heated at refluxing under argon until the solution became clear (3 hours). Excess HMDS was removed under reduced pressure and the residue was dried under high vacuum for 3 hours. The oily residue was dissolved in dry methylene chloride (20 ml) and a solution of 2-benzoyloxymethyl-4-acetoxy-1, 3-oxathiolane (example 4) (748 mg) in dry methylene chloride (15 ml). The reaction mixture was stirred overnight at room temperature (20 hours) then poured into saturated aqueous NaHCO$_3$-solution (100 ml). The organic layer was collected and the aqueous phase was extracted with methylene chloride (2×50 ml). The combined organic phase was washed with water, dried over MgSO$_4$, filtered and evaporated under reduced pressure. The residue was purified and separated by chromatography on silica gel using hexane-:ethyl acetate (1:4) as eluant. It gave 258 mg (29%) of a fast moving product, which was identified as trans-isomer and 156 mg (18%) of a low moving product, which was identified as cis-isomer.

cis-isomer:

$^1$H-NMR: δ(ppm in DMSO d$_6$) 11.39 (s, 1H, N$_3$—H), 8.00 (d, 2H, aromatic), 7.97 (m, 2H, C$_6$·—H and aromatic), 7.56 (m, 2H, aromatic), 6.31 (d, 1H, C$_4$—H), 5.53 (t, 1H, C$_2$—H), 5.41 (d, 1H, C$_5$—H), 4.76 (d, 2H, C$_2$—C$_2$OH), 4.65 (d, 1H, C$_5$—H), 4.01 (dd, 1H, C$_5$—H), $^{13}$C-NMR: δ(ppm in DMSO d$_6$). 165.83, 163.36, 151.06, 141.25, 134.15, 129.72, 129.50, 129.29, 102.83, 85.34, 76.60, 63.78 and 62.68.

trans-isomer:

$^1$H-NMR: δ(ppm in CDCl$_3$) 9.10 (b, 1H, N$_3$·—H), 8.02 (d, 2H, aromatic), 7.53 (m, 2H, C$_6$·—H and aromatic), 7.43 (m, 2H, aromatic), 6.50 (d, 1H, C$_4$—H), 5.87 (dd, 1H, C2$_5$·—H), 5.76 (d, 1H, C$_5$—H), 4.56 (dd, 1H, C$_2$—CH$_2$OBz), 4.30 (m, 2H, C$_5$—H), 4.24 (dd, 1H, C$_2$—H$_2$OBz), $^{13}$C-NMR: δ(ppm in CDCl$_3$) 166.28, 163.49, 150.89, 140.70, 133.59, 129.87, 129.42, 128.64, 103.72, 84.18, 75.18, 64.24 and 62.23.

Example 9

CIS- AND TRANS-2-HYDROXYMETHYL-4-(URACIL-1'-YL)-1,3-OXATHIOLANE

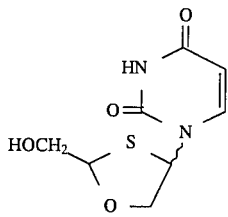

(XXXV)

cis-isomer:

A solution of cis-2-benzoyloxymethyl-4-(uracil-1'-yl)-1, 3-oxathiolane (example 8) (150 mg) in methanolic ammonia (50 ml) was stirred overnight at room temperature (16 hours). Solvent was evaporated in vacuo and the residue was triturated with ether (2×10 ml) and crystallized in ethyl acetate to yield 77 mg (75%) of desired product which was characterized by spectroscopic methods.

m.p.: 138°–140° C.

UV: (CH$_3$OH) Lamda max: 266 nm $^1$H-NMR: δ(ppm in DMSO d$_6$) 11.36 (s, 1H, N$_3$·—H), 7.88 (d, 1H, C$_6$·—H), 6.28 (d, 1H, C$_4$—H), 5.66 (d, 1H, C$_5$·—H), 5.39 (t, 1H, C$_2$—C$_2$OH), 5.19 (t, 1H, C$_2$—H), 4.55 (d, 1H, C$_5$—H), 3.95 (dd, 1H, C$_5$—H), 3.80 (m, 2H, C$_2$—CH$_2$OH).

$^{13}$C-NMR: δ(ppm in DMSO d$_6$). 163.54, 151.13, 141.87, 102.63, 89.13, 77.15, 62.45 and 62.04.

trans-isomer:

A solution of trans-2-benzoyloxymethyl-4-(uracil-1'-yl)-1,3-oxathiolane (example 8) (207 mg) in methanolic ammonia (50 ml) was stirred overnight at room temperature (16 hours) and then evaporated in vacuo. The residue was treated with ether (2×20 ml) and filtered. The solid residue was washed with cold ethyl acetate and yield 115 mg (81%) of pure product which was characterized by $^1$H- and $^{13}$C-NMR.

m.p.: 176°–178° C.

UV: (CH$_3$OH) Lamda max: 266 nm.

$^1$H-NMR: δ(ppm in DMSO d$_6$) 11.39 (s, 1H, N$_3$·—H), 7.66 (d, 1H, C$_6$·—H), 6.25 (d, 1H, C$_4$—H), 5.67 (d, 1H, C$_5$·—H), 5.62 (dd, 1H, C$_2$—H), 5.27 (t, 1H, C$_2$—C$_2$OH), 4.35 (d, 1H, C$_5$—H), 4.16 (dd, 1H, C$_5$—H), 3.60 (m, 1H, C$_2$—CH$_2$OH), 3.35 (m, 1H, C$_2$—C$_2$OH).

$^{13}$C-NMR: δ(ppm in DMSO d$_6$) 163.53, 151.15, 141.77, 102.78, 87.77, 74.28, 63.25 and 62.32.

Example 10

CIS- AND TRANS-2-BENZOYLOXYMETHYL-4-(THYMIN-1'-YL)-1,3-OXATHIOLANE

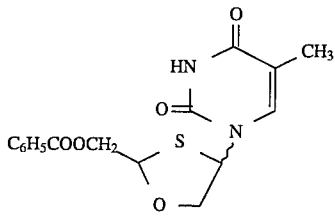

(XXXVI)

A mixture of thymine (671 mg), ammonium sulfate (20 mg) and hexamethyldisilazane (HMDS, 20 ml) was heated at refluxing until the solution became clear (3 hours). Excess reagent was evaporated in vacuo and the remaining volatile removed under high vacuum (1 hour). The oily residue was dissolved in dry methylene chloride (20 ml) and a solution of 2-benzoyloxymethyl-4-acetoxy-1,3-oxathiolane (example 4) (1.05 g) in dry methylene chloride (20 ml) was added under argon, followed by a solution of trimethylsilyl trifluoromethane sulfonate (865 ml) in methylene chloride (5 ml). The reaction mixture was stirred overnight at room temperature under argon (16 hours) and poured into saturated aqueous $NaHCO_3$-solution. The organic layer was separated and the aqueous phase extracted with methylene chloride (3×50 ml). The combined organic layer was washed with water (2×50 ml). The combined organic layer was washed first with water (2×50 ml), then with brine solution (100 ml), dried over $MgSO_4$, filtered and evaporated in vacuo. The residue was purified and separated by chromatography on silica gel using hexane:ethyl acetate (1:1) as eluant to give 732 mg of a fast moving product which was identified by spectroscopic methods as trans-isomer and 244 mg of a lower moving product which was identified as cis-isomer.

Total yield was 976 mg (75%).

cis-isomer:

$^1$H-NMR: δ(ppm in DMSO $d_6$) 11.41 (s, 1H, $N_{3'}$—H), 7.98 (d, 2H, aromatic), 7.72 (t, 1H, aromatic), 7.53 (t, 2H, aromatic), 7.47 (s, 1H, $C_{6'}$—H), 6.32 (d, 1H, $C_2$—H), 4.73 (m, 3H, $C_5$—H and $C_2$—$CH_2OOCC_6H_5$), 4.01 (dd, 1H, $C_5$—H), 1.58 (s, 3H, $CH_3$).

$^{13}$C-NMR: δ(ppm in DMSO $d_6$) 165.89, 164.00, 151.08, 136.37, 134.09, 129.63, 110.73, 85.30, 75.99, 63.68, 62.58 and 12.18.

trans-isomer:

$^1$H-NMR: δ(ppm in $CDCl_3$) 8.30 (s, 1H, $N_{3'}$—H), 8.04 (d, 2H, aromatic), 7.58 (t, 1H, aromatic) 7.45 (t, 2H, aromatic), 7.32 (d, 1H, $C_{6'}$—H, J=1.3 Hz), 6.50 (dd, 1H, $C_4$—H), 5.90 (dd, 1H, $C_2$—H), 4.58 (dd, 1H $C_2$—$C_2OCC_6H_5$), 4.30 (m, 2H, $C_5$—H), 4.24 (dd, 1H, $C_2$—$CH_2OOCC_6H_5$), 1.91 (d, 3H, —$CH_3$, J=1.1 Hz).

$^{13}$C-NMR: δ(ppm in $CDCl_3$) 166.29, 163.91, 150.95, 136.14, 133.59, 129.88, 128.58, 112.48, 84.16, 75.04, 64.29, 62.35 and 12.41.

Example 11

CIS- AND TRANS-2-HYDROXYMETHYL-4-(THYMIN-1'-YL)-1,3-OXATHIOLANE

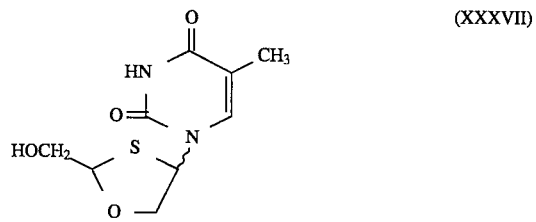

cis-isomer:

A solution of cis-2-benzoyloxymethyl-4-(thymin-1'-yl)-1,3-oxathiolane (example 10) (190 mg) in saturated methanolic ammonia was stirred overnight at room temperature (16 hours). The mixture was evaporated under reduced pressure and the residue was purified by chromatography on silica gel using ethyl acetate as eluant to give 109 mg (82%) of pure product.

m.p.: 149°–151° C.

UV: ($CH_3OH$) Lamda max: 271.3 nm.

$^1$H-NMR: δ(ppm in DMSO $d_6$) 11.37 (s, 1H, $N_{3'}$—H, $D_2O$-exchange), 7.79 (d, 1H, $C_{6'}$—H, J=1.1 Hz), 6.30 (d, 1H, $C_4$—H, J=4.4 Hz), 5.44 (t, 1H, $C_2$—$C_2OH$, $D_2O$-exchange), 5.20 (t, 1H, $C_2$—H, J=4.2 Hz), 4.52 (d, 1H, $C_5$—H, J=10.7 Hz), 3.93 (dd, 1H, $C_5$—H, J=4.90 and 10.7 Hz), 3.81 (m, 2H, $C_2$—$C_2OH$), 1.78 (s, 3H, —$CH_3$).

$^{13}$C-NMR: δ(ppm in DMSO $d_6$) 164.15, 151.08, 137.44, 110.14, 89.09, 67.17, 62.18, 61.89 and 12.37.

trans-isomer:

A mixture of trans-2-benzoyloxymethyl-4-(thymin-1'-yl)-1,3-oxathiolane (example 10) (200 mg) in saturated methanolic ammonia (50 ml) was stirred overnight at room temperature (16 hours). The mixture was evaporated under reduced pressure and the residue was triturated with diethyl ether (3×15 ml) and filtered. The solid residue was recrystallized in ethanol to give 136 mg (97%) of pure product.

m.p.: 202°–204° C.

UV: ($CH_3OH$) Lamda max: 271.3 nm.

$^1$H-NMR: δ(ppm in DMSO $d_6$), 1.40 (s, 1H, $N_{3'}$—H, $D_2O$ exchange), 7.49 (s, 1H, $C_{6'}$—H), 6.26 (d, 1H, $C_4$—H), 5.67 (dd, 1H, $C_2$—H), 5.27 (t, 1H, $C_2$—$C_2OH$, $D_2O$-exchange), 4.32 (d, 1H, $C_5$—H), 4.16 (dd, 1H, $C_5$—H), 3.58 (dd, 1H, $C_2$—$C_2OH$), 3.33 (dd, 1H, $C_2$—$CH_2OH$), 1.80 (s, 3H, $CH_3$).

$^{13}$C-NMR: δ(ppm in DMSO $d_6$).

Example 12

2-BENZOYLOXYMETHYL-1,3-DITHIOLANE

A mixture of 2-benzoyloxyacetaldehyde (example (5.65 g), 1,2-ethanedithiol (3 ml) and paratoluenesulfonic acid (200 mg) in toluene (250 ml) was heated at refluxing under water removal conditions using a Dean Stark apparatus for 4 hours. The mixture was cooled to room temperature, washed first with saturated aqueous $NaHCO_3$ solution (1×60 ml), then with water (2×60 ml), and dried over reduced pressure. The residue was purified by chromatography on silica gel using hexane:ethyl acetate (9:1) as eluant to give 5.2 g of pure product which was characterized by $^1$H- and $^{13}$C-NMR spectroscopy.

$^1$H-NMR:δ(ppm in $CDCl_3$) 8.07 (m, 2H, aromatic), 7.59 (m, 1H, aromatic), 7.44 (m, 2H, aromatic), 4.75 (t, 1H, $C_2$—H), 4.36 (d, 2H, $C_2$—$CH_2OOCC_6H_5$) 3.24 (s, 4H, $C_4$—H and $C_5$—H), $^{13}$C-NMR: δ(ppm in $CDCl_3$) 166.27, 133.30, 129.85, 128.53, 68.15, 50.46 and 37.87.

Example 13

2-BENZOYLOXYMETHYL-3-OXO-1,3-DITHIOLANE

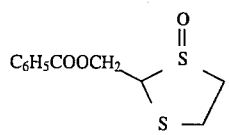
(XX)

2-Benzoyloxymethyl-1,3-dithiolane (example 12) (5.2 g) was dissolved in dry methylene chloride (200 ml) and cooled to 0° C. in an ice bath. Meta-chloroperbenzoic acid (80%, 4.67 g) in methylene chloride (100 ml) was added slowly while under stirring. The mixture was stirred at room temperature for 1 hour and then poured with into saturated aqueous $NaHCO_3$ solution (100 ml). The organic layer was separated, washed first with saturated $NaHCO_3$ solution (2×100 ml), then with water (100 ml), and finally with brine solution (100 ml), dried over $MgSO_4$ and filtered. The filtrate was evaporated in vacuo and the residue purified by chromatography on silica gel using ethyl acetate as eluant to give 4.0 g (74%) of pure product as a mixture cis- and trans-isomers.

$^1$H-NMR: δ(ppm in $CDCl_3$) 8.09 (m, 2H, aromatic), 7.60 (m, 1H, aromatic), 7.46 (m, 2H, aromatic), 4.82 (dd, 1H, $C_2$—H, trans-isomers), 4.57 (m, 2H, $C_2$—$CH_2OOCC_6H_5$) 4.32 (dd, 1H, $C_2$—H, cis-isomer), 3.78 (m, 1H, $C_4$—H, trans-isomer), 3.59 (m, 2H, $C_5$—H, cis- and trans-isomer), 3.41 (m, 1H, $C_4$—H, cis-isomer), 2.87 (m, 1H, $C_4$—H, cis- and trans-isomer).

Example 14

CIS- AND TRANS-2-BENZOYLOXYMETHYL-4-ACETOXY-1,3-DITHIOLANE

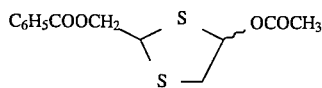
(XXI)

A mixture of 2-benzoyloxymethyl-3-oxo-1,3-dithiolane (example 13) (5.1 g), sodium acetate (65 g) and acetic anhydride (100 ml) was heated at refluxing for 3 hours. Excess reagent was removed under reduced pressure. The residue was dissolved in methylene chloride (200 ml), washed first with saturated aqueous $NaCO_3$ solution (3×100 ml), then with water (100 ml), and finally with brine solution (100 ml), dried over $MgSO_4$, and filtered. The filtrate was evaporated in vacuo and the residue purified by chromatography on silica gel using hexane:ethyl acetate (9:1) as eluant. The desired product was a byproduct and obtained in 9% yield (535 mg) as a mixture cis- and trans-isomer which was characterized by spectroscopic methods.

cis-isomer:

$^1$H-NMR: δ(ppm in $CDCl_3$) 8.01 (m, 2H, aromatic), 7.54 (m, 1H, aromatic), 7.41 (m, 2H, aromatic), 6.51 (t, 1H, $C_4$—H), 4.79 (t, 1H, $C_2$—H), 4.39 (dd, 1H, $C_2$—$CH_2OOCC_6H_5$), 4.26 (dd, 1H, $C_2$—$CH_2OOCC_6H_5$), 3.34 (m, 2H, $C_5$—H), 2.05 (s, 3H, $CH_3$).

trans-isomer:

$^1$H-NMR: δ(ppm in $CDCl_3$) 8.04 (m, 2H, aromatic), 7.57 (m, 1H, aromatic), 7.42 (m, 2H, aromatic), 6.56 (t, 1H, $C_4$—H), 4.85 (t, 1H, $C_2$—H), 4.53 (m, 2H, $C_2$—$CH_2OOCC_6H_5$) 3.48 (d, 2H, $C_5$—H), 2.08 (s, 3H, $CH_3$).

Example 15

CIS- AND TRANS-2-BENZOYLOXYMETHYL-4-(CYTOSIN-1'-YL)-1,3-DITHIOLANE

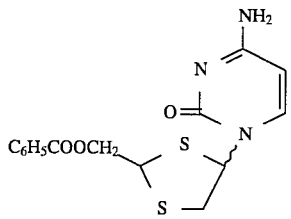
(XXII)

A mixture of cytosine (500 mg), ammonium sulfate (20 mg) and hexamethyldisilazane (15 ml) was heated at refluxing under argon until the solution became clear (3 hours). Excess reagent was evaporated under reduced pressure. The residue was dried under high vacuum for 1 hour and dissolved in dry methylene chloride (40 ml). A solution of 2-benzoyloxymethyl-4-acetoxy-1,3-dithiolane (example 14) (882 mg) in dry methylene chloride (30 ml) was added under argon and the mixture was cooled at −10° C. in an ice-salt bath. A solution of $SnCl_4$ (0.52 ml) in methylene chloride (50 ml) was added and the mixture was stirred for 30 minutes and then heated overnight at refluxing (16 hours). The mixture was cooled to room temperature and poured into aqueous $NaHCO_3$ solution (100 ml). The organic layer was collected and the aqueous layer extracted with methylene chloride (2×100 ml) and filtered over celite. The combined organic layer was washed with water (2×100 ml), dried over $MgSO_4$, filtered and evaporated under reduced pressure. The residue was purified by chromatography on silica gel using ethyl acetate:methanol (9:1) as eluant to give 335 mg (32%) of the product in as a mixture of cis- and trans-isomers in a ratio of 1:1.2. The product was separated in next step as N-acetyl derivatives.

Example 16

CIS- AND TRANS-2-BENZOYLOXYMETHYL-4-(N4'-ACETYLCYTOSIN-1'-YL)-1,3-DITHIOLANE

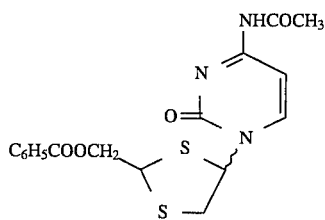
(XXIII)

A solution cis- and trans-2-benzoyloxymethyl-4-(cytosin-1'-yl)-1,3-dithiolane (example 15) (170 mg), 4-dimethylaminopyridine (20 mg), and acetic anhydride (0.1 ml) in dry pyridine (15 ml) was stirred overnight at room temperature (16 hours) and then poured into cold water (100 ml). The mixture was extracted with methylene chloride (3×75 ml), and the combined organic layer was washed with water (3×100 ml), dried over $MgSO_4$ and filtered. The filtrate was evaporated in vacuo and the residue was purified by chromatography on silica gel using ethyl acetate as eluant to give pure trans-2-benzoyloxymethyl-4-(N4'-acetyl cytosin-1'- yl)-1,3-dithiolane as the fast moving spot and pure cis-2-benzoyloxymethyl-4-(N4'-acetyl cytosin-1'-yl)-1,3-dithiolane as the lower moving product. The two isomers were characterized by spectroscopic methods.

cis-isomer:

$^1$H-NMR: δ(ppm in CDCl$_3$) 9.51 (s, 1H, C$_{4'}$—NH—COCH$_3$), 8.49 (d, 1H, C$_{6'}$—H, J=7.6 Hz), 8.04 (m, 2H, aromatic), 7.60 (m, 1H, aromatic), 7.45 (m, 2H, aromatic), 7.29 (d, 1H, C$_{5'}$—H, J=7.6 Hz), 6.70 (d, 1H, C$_4$—H, J=1.7 Hz), 4.99 (t, 1H, C$_2$—H, J=2.6 Hz), 4.76 (m, 2H, C$_2$—CH$_2$OOCC$_6$H$_5$) 3.61 (dd, 1H, C$_5$—H, J=4.2 and 13.5 Hz), 3.45 (d, 1H, C$_5$—H, J=13.2 Hz), 2.25 (s, 3H, CH$_3$).

trans-isomer:

$^1$H-NMR: δ(ppm in CDCl$_3$) 9.50 (s, 1H, C$_{4'}$—NH—COCH$_3$), 8.24 (d, 1H, C$_{6'}$—H, J=7.6 Hz), 8.03 (m, 2H, aromatic), 7.61 (m, 1H, aromatic), 7.46 (m, 3H, C$_{5'}$—H and aromatic), 6.76 (d, 1H, C$_4$—H, J=3.6 Hz), 5.02 (t, 1H, C$_2$—H, J=7.2 Hz), 4.49 (dd, 1H, C$_2$—CH$_2$OOCC$_6$C$_5$, J=7.1 and 11.4 Hz), 4.37 (dd, 1H, C$_2$—CH$_2$OOCC$_6$H$_5$, J=7.2 and 11.4 Hz), 3.62 (dd, 1H, C$_5$—H, J=4.2 and 13 Hz), 3.43 (d, 1H, C$_5$—H, J=14.5 Hz), 2.26 (s, 3H, CH$_3$).

Example 17

CIS- AND TRANS-2-HYDROXYMETHYL-4-(CYTOSIN-1'-YL)-1,3-DITHIOLANE

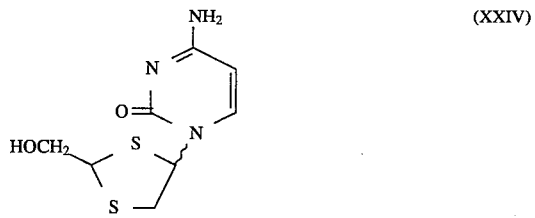 (XXIV)

cis-isomer (BCH-373):

A solution of cis-2-benzoyloxymethyl-4-(N4'-acetylcytosin-1'-yl)-1,3-dithiolane (example 16) (10 mg) in methanolic ammonia (20 ml) was overnight stirred at room temperature (16 hours). The mixture was evaporated under reduced pressure and the residue purified by chromatography on silica gel using ethyl acetate:methanol (4:1) as eluant to give 3 mg (47%) of the desired product as a foam.

trans-isomer:

A solution of trans-2-benzoyloxymethyl-4-(N4'-acetylcytosin-1'-yl)-1,3-dithiolane (example 16) (35 mg) in methanolic ammonia (20 ml) was stirred overnight at room temperature. The mixture was evaporated under reduced pressure and the residue was triturated with diethyl ether (2×10 ml) to give the desired product in yield.

m.p.: 198°–200° C.

UV: (CH$_3$OH) Lamda max: 270 nm $^1$H-NMR: δ(ppm in DMSO d$_6$): 7.91 (d, 1H, C$_6$—H, J=7.5 Hz), 7.19 (d, 2H, C$_4$—NH$_2$, D$_2$O-exchange), 6.49 (d, 1H, C$_4$—H, J=3.0 Hz), 5.71 (d, 1H, C$_5$—H, J=7.5 Hz), 5.38 (t, 1H, C$_2$—CH$_2$OH, D$_2$O-exchange), 4.75 (t, 1H, C$_2$—H, J=6.9 Hz), 3.40 (m, 4H, C$_5$—H and C$_2$—CH$_2$OH), $^{13}$C-NMR: δ(ppm in DMSO d$_6$): 171.60, 160.93, 148.39, 98.86, 73.64, 71.56, 60.66 and 48.01.

Example 18

CIS AND TRANS-BENZOYLOXYMETHYL-4-BENZOYLOXY-1,3-OXATHIOLANE

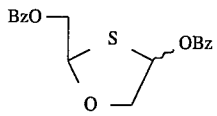

2-Benzoyloxy-1,3-oxathiolane (0.4 g, 1.78 mmol) was dissolved in 200 mL of degased dry benzene under a stream of argon. To this solution was added benzoyl peroxide (0.863 g, 3.56 mmol) and AIBN catalyst (15 mg, 0.09 mmol, 5%) in one portion. The resulting mixture was refluxed for 4 hours under argon. The solvent was then removed under high vacuum, and the residue was dissolved in dichloromethane (40 ml), extracted 2X with a solution of 10% sodium bicarbonate (15 mL) and dried over MgSO$_4$. Evaporation of dichloromethane under reduced pressure and purification of the residue on silica gel column using ethyl acetate; hexane (30%) as eluant afforded the pure mixture of cis- and trans-1,3-oxathiolane derivative as a colorless oil (264 mg, 0.76 mmol, 43% yield). The trans isomer was separated as a white solid m.p. 60°–62° C. This mixture was fully characterized by $^1$H, and $^{13}$C NMR spectrum. R$_f$=0.43 (ethyl acetate: hexanes 1:4).

$^1$H NMR δ(ppm in CDCl$_3$): 8.07 (m, 2H, aromatic), 7.59 (m, 1H, aromatic), 7.56 (m, 2H, aromatic), 6.51 (t, 1H, C$_4$—H), 5.79 (m, 1H, C$_2$—H), 4.63 (m, 2H, CH$_2$—OCOPh), 4.32 (m, 2H, C$_5$—H). 13C NMR δ(ppm in CDCl$_3$): 166.56, 166.36, 134.12, 133.78, 130.35, 129.04, 84.40, 82.53, 75.04, 65.33, 39.89, 25.43, 23.93.

Example 19

CIS AND TRANS-2-BENZOYLOXYMETHYL-4-(5'-FLUOROCYTOSIN-1'-YL)-1,3-OXATHIOLANE

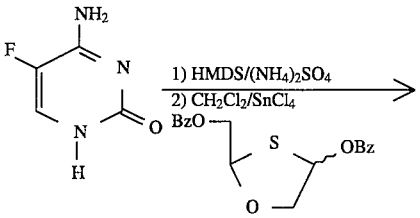

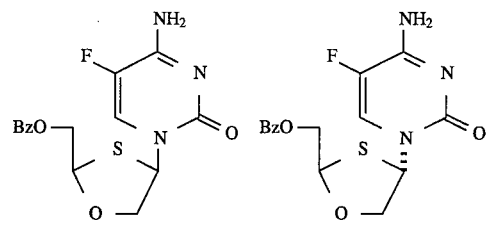

5-fluorocytosine (700 mg, 5.4 mmol) was heated at reflux HMDS(1,1,1,3,3,3-hexamethyldisilazane, 30 ml) containing catalytic amount of ammonium sulfate (20 mg) for overnight (16 h). The clear solution was evaporated to dryness under reduced pressure and the residue was dissolved in dry methylene chloride (50 ml). To this solution was added through a cannula a mixture of 2-benzoyloxymethyl-4-benzoyloxy-1,3-oxathiolane (example 18) (1.25 g, 3.63 mmol) in dry methylene chloride (50 ml), followed by adding tin tetrachloride (4 ml of 1M solution in methylene chloride). The reaction mixture was stirred under argon atmosphere at room temperature for 16h and heated at reflux for 1 h. After cooling to room temperature the mixture was poured into saturated aqueous NaHCO$_3$ solution (150 ml), stirred for 15 min. and filtered over celite. The organic layer was collected. The aqueous solution was further extracted with methylene chloride (2×100 ml). The combined organic phase was washed twice with water (2×150 ml), once with brine solution, dried over Na$_2$SO$_4$, and filtered. Solvent was removed under reduced pressure. The residue contained two compounds in a ratio of 2:3 for cis and trans isomers and was purified on silica gel using ethyl acetate-methanol 95:5 as eluant to give 280 mg of cis isomer and 420 mg of trans isomer for a total yield of 53%.

Cis isomer:

Mp.: 235°–236° C. (dec.).

R$_f$: 0.36 (EtOAc:MeOH 9:1).

$^1$H-NMR (300 MHz, DMSO-d$_6$): δin ppm: 7.94 (m, 2H, aromatic), 7.80 (d, 2H, H-6' and 1H of NH$_2$ underneat, J$_{H-F}$=6.8 Hz), 7.68 (m, 1H, aromatic), 7.58 (b, 1H of NH$_2$), 7.47 (m, 2H, aromatic), 6.28 (d, 1H, H-4, J=3.0 Hz), 5.51 (t, 1H, H-2, J=3.8 Hz), 4.73 (m, 2H, —CH$_2$OBz), 4.61 (d, 1H, H-5, J=11 Hz) and 3.98 (dd, 1H, H-5, J=4.7 and 11 Hz).

Trans-isomer:

Mp.: 235°–236° C. (dec.).

$^1$H-NMR (300 MHz, DMSO-d$_6$): δin ppm: 7.97 (m, 2H, aromatic), 7.81 (d, 2H, H-6' and 1H of NH$_2$ underneat, J$_{H-F}$=7.1 Hz), 7.66 (m, 1H, aromatic), 7.55 (m, 3H, 2H of aromatic and 1H of NH$_2$), 6.32 (d, 1H, H-4, J=4.8 Hz), 6.02 (dd, 1H, H-2, J=3.2 and 8.5 Hz), 4.55 (dd, 1H, —CH$_2$OBz, J=8.4 and 11.9 Hz), 4.38 (d, 1H, H-5, J=10.2 Hz) and 4.26 (dd, 2H, 1H of H-5 and 1H of —CH$_2$OBz, J=3.6 and 10.5 Hz).

Example 20

CIS-2-HYDROXYMETHYL-4-(5'-FLUOROCYTOSIN-1'-YL)-1,3-OXATHIOLANE (BCH-1081)

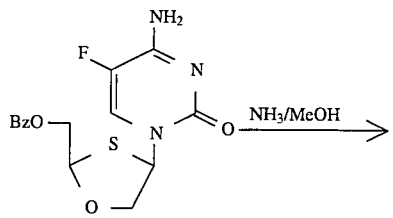

Cis-2-benzoyloxymethyl-4-(5'-fluorocytosin-1'-yl)-1,3-oxathiolane (example 19) (75 mg , 0.21 mmol) was dissolved in methanolic ammonia (25 ml). The mixture was stirred at room temperature for 16 h and solvents were removed under reduced pressure. The residue was triturated with ether (2×20 ml). The remaining solid was recrystallized in ethanol-ether to give the desired compound (43 mg) in 80% yield.

M.p.: >210° C. (dec.)

R$_f$: 0.41 (EtOAc:MeOH 4:1)

UV: λ$_{max}$ (H$_2$O): 284 nm $^1$H-NMR (300 MHz, DMSO-d$_6$): δin ppm: 8.14 (d, 1H, H-6', J$_{H-F}$=7.1 Hz), 7.79 (bs, 1H, NH$_2$, D$_2$O exchangable), 7.56 (bs, 1H, NH$_2$, D$_2$O exchangable), 6.28 (d, 1H, H-4, J=2.6 Hz), 5.44 (t, 1H, OH, D$_2$O exchangable), 5.18 (t, 1H, H-2, J=5.5 Hz), 4.44 (d, 1H, H-5, J=10.5 Hz), 3.91 (dd, 1H, H-5, J=4.6 and 10.6 Hz), and 3.78 (m, 2H, CH$_2$OH).

Example 21

(1'R,2'S,5'R)-MENTHYL-1,3-OXATHIOLAN-2S-CARBOXYLATE

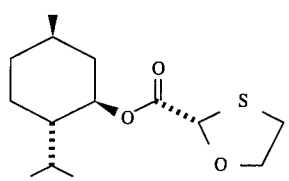

To a mixture of (1'R,2'S,5'R)-menthyl-5S-acetoxy-1,3-oxathiolan-2S-carboxylate (WO 92/20669, enclosed herewith by reference) (1.0 g, 3.03 mmol) and triethylsilane (4.84 ml, 30.3 mmol) at room temperature under an argon atomosphere was added trimethylsilyl trifluoromethanesulfonate (0.584 ml, 3.03 mmol ). The reaction mixture was stirred at room temperature for 12 h and then diluted with dichloromethane (150 ml), washed with saturated aqueous solution of NaHCO$_3$, water, brine, dried over sodium sulfate and concentrated.

Chromatography (Hexane-EtOAc, 6:1) of the crude product gave the product (0.71g, 87%) as colourless oil: $^1$H NMR in CDCl$_3$: δ0.45–2.10 (m, 17H), 2.96–3.20 (m, 2H), 4.20–4.40 (m, 2H), 4.72 (dt, 1H), 5.45 (s, 1H); [α]$_D^{25}$ −102.9° (c, 1.02, CHCl$_3$).

Example 22

(1'R,2'S,5'R )-MENTHYL-1,3-OXATHIOLAN-2R-CARBOXYLATE

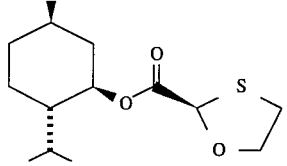

To a mixture of (1'R,2'S,5'R)-menthyl-5S-acetoxy-1,3-oxathiolan-2R-carboxylate (WO 92/20669) (0.50 g, 1.51 mmol) and triethylsilane (2.42 ml, 15.1 mmol) at room temperature under an argon atomosphere was added trimethylsilyl trifluoromethanesulfonate (0.29 ml, 1.51 mmol). The reaction mixture was stirred at room temperature for 12 h and then diluted with dichloromethane (125 ml), washed with saturated aqueous solution of NaHCO$_3$, water, brine, dried over sodium sulfate and concentrated. Chromatography (Hexane-EtOAc, 6:1) of the crude product gave the product (0.369 g, 86%) as colourless oil: $^1$H NMR in CDCl$_3$: δ0.40–2.10 (m, 17H), 2.98–3.19 (m, 2H), 4.20–4.40 (m, 2H), 4.72 (dt, 1H), 5.46 (s, 1H).

Example 23

2R-HYDROXYMETHYL-1,3-OXATHIOLANE

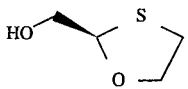

To a solution of (1'R,2'S,5'R)-menthyl-1,3-oxathiolan-2R-carboxylate (example 22) (3.23 g, 11.9 mmol) in anhydrous ethanol (20 ml) at 0° C. under an argon atmosphere were added sodium borohydride (1.12 g, 29.7 mmol) and anhydrous methanol (0.916 ml, 47.6 mmol). The reaction mixture was stirred at 0° C. for 1 h and allowed to warm to room temperature and stirred for 12 h. The reaction was then quenched with acetic acid and the solvent was removed in vacuo. The obtained residue was diluted with dichloromethane (225 ml), washed with water, brine, dried over sodium sulfate and concentrated. Chromatography (Hexane-Et$_2$O, 1:1) of the crude product gave the product (1.30 g, 91%) as colourless oil: $^1$H NMR in CDCl$_3$ δ2.85–2.97 (m, 2H), 3.58 (dd, 1H, J=12.2, 5.4Hz), 3.66 (dd, 1H, J=12.2, 3.3Hz), 3.75–3.85 (m, 1H), 4.14–4.25 (m, 1H), 5.16 (dd, 1H, J=5.4, 3.3Hz).

Example 24

2S-HYDROXYMETHYL-1,3-OXATHIOLANE

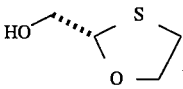

To a solution of (1'R,2'S,5'R)-menthyl-1,3-oxathiolan-2S-carboxylate (example 21) (1.16 g, 4.26 mmol) in anhydrous ethanol (10 ml) at 0° C. under an argon atmosphere were added sodium borohydride (0.403 g, 10.7 mmol) and anhydrous methanol (0.690 ml, 17.03 mmol). The reaction mixture was stirred at 0° C. for 1 h and allowed to warm to room temperature and stirred for 12 h. The reaction was then quenched with acetic acid and the solvent was removed in vacuo. The obtained residue was diluted with dichloromethane (150 ml), washed with water, brine, dried over sodium sulfate and concentrated. Chromatography (Hexane-Et$_2$O, 1:1) of the crude product gave the product (0.47 g, 92%) as colourless oil: $^1$H NMR in CDCl$_3$: δ2.85–2.99 (m, 2H), 3.60 (dd, 1H, J=12.2, 5.5Hz), 3.65 (dd, 1H, J=12.2, 3.3Hz), 3.80–3.90 (m, 1H), 4.20–4.30 (m, 1H), 5.15 (dd, 1H, J=5.5, 3.3Hz); [α]$_D^{25}$ –35.6° (c, 1.25, CHCl$_3$).

Example 25

2S-t-BUTYLDIPHENYLSILYLOXYMETHYL-1,3-OXATHIOLANE

To a solution of 2S-hydroxymethyl-1,3-oxathiolane (example 24) (0.63 g, 5.3 mmol), imidazole (0.71 g, 10.4 mmol) in tetrahydrofuran (15 ml) at 0° C. under an argon atomosphere was added a solution of t-butyldiphenylsilyl chloride (2.16 g, 7.9 mmol) in tetrahydrofuran (8 ml). The reaction mixture was allowed to warm to room temperature and stirred for 12 h then diluted with dichloromethane (125 ml). The organic layer was washed with water, brine, dried over sodium sulfate and concentrated. Chromatography (Hexane-EtOAc, 6:1) of the crude product gave the product (1.87 g, 99%) as colourless oil: $^1$H NMR in CDCl$_3$: δ1.08 (s, 9H), 2.93–2.99 (m, 2H), 3.70 (dd, 1H, J=10.9, 4.6Hz), 3.86 (dd, 1H, J=10.9, 6.4Hz), 3.94–4.15 (m, 2H), 5.29 (dd, 1H, J=6.4, 4.6Hz), 7.35–7.50 (m, 6H), 7.68–7.75 (m, 4H), [α]$_D^{25}$ –23.3° (c, 1.0, CHCl$_3$).

Example 26

2R-t-BUTYLDIPHENYLSILYLOXYMETHYL-1,3-OXATHIOLANE

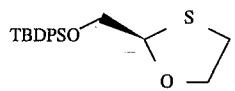

To a solution of 2R-hydroxymethyl-1,3-oxathiolane (example 23) (1.30 g, 10.8 mmol), imidazole (1.47 g, 21.6 mmol) in tetrahydrofuran (30 ml ) at 0° C. under an argon atomosphere was added a solution of t-butyldiphenylsilyl chloride (4.46 g, 16.2 mmol) in tetrahydrofuran (15 ml). The reaction mixture was allowed to warm to room temperature and stirred for 12 h, then diluted with dichloromethane (150 ml). The organic layer was washed with water, brine, dried over sodium sulfate and concentrated. Chromatography (Hexane-EtOAc, 6:1) of the crude product gave the product (3.64 g, 94%) as colourless oil: $^1$H NMR in CDCl$_3$: δ1.04 (s, 9H), 2.89–2.99 (m, 2H), 3.65 (dd, 1H, J=10.9, 4.6Hz), 3.88 (dd, 1H, J=10.9, 6.4Hz), 3.90–4.14 (m, 2H), 5.27 (dd, 1H, J=6.4, 4.6Hz), 7.34–7.46 (m, 6H), 7.64–7.74 (m, 4H).

Example 27

TRANS AND CIS-2R-t-BUTYLDIPHENYLSILYLOXYMETHYL-4-ACETOXY-1,3-OXATHIOLANE

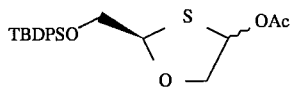

Solid meta-chloroperbenzoic acid (MCPBA) (0.23 g, 80%, 1.06 mmol) was added to a stirred solution of 2R-t-butyldiphenylsiloxy methyl-1,3-oxathiolane (example 26) (0.32 g, 0.89 mmol) in dichloromethane (20 ml) at 0° C. The reaction mixture was stirred at 0° C. for 2 h and then diluted with dichloromethane (150 ml), washed with saturated aqueous Na$_2$CO$_3$ solution, water, brine, dried over sodium sulfate and concentrated. Chromatography of the crude product gave a mixture of sulfoxides. The mixture of the obtained sulfoxide, acetic anhydride (10 ml), tetrabutyl ammonium acetate (0.32 g , 1.06 mmol) was then heated at 120° C. for 6 h and the excess acetic anhydride was removed in vacuo. The residue was diluted in dichloromethane (150 ml), washed with water, brine, dried over sodium sulfate and concentrated. Chromatography of the crude product gave a mixture of acetate (0.164 g, 45%) as colourless oil: ¹H NMR in CDCl₃: δ1.05 (s, 9H), 2.03 (s, 1.35H), 2.08 (s, 1.65H), 3.60–4.50 (m, 4H), 5.28 (t, 0.45H, J=5.4 Hz), 5.55 (dd, 0.55H, J=6.5, 4.7 Hz), 6.14–6.20 (m, 1H), 7.30–7.50 (m, 6H), 7.60–2.78 (m, 4H).

Example 28

TRANS AND CIS-2S-t-BUTYLDIPHENYLSILYLOXYMETHYL-4-ACETOXY-1,3-OXATHIOLANE

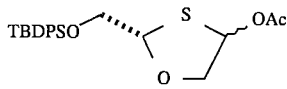

Solid MCPBA (0.85 g, 80%, 3.9 mmol) was added to a stirred solution of 2S-t-butyldiphenylsiloxymethyl-1,3 -oxathiolane (example 25) (1.35 g, 3.9 mmol) in dichloromethane (30 ml) at 0° C. The reaction mixture was stirred at 0° C. for 2 h and then diluted with dichloromethane (225 ml), washed with saturated aqueous Na₂CO₃ solution, water, brine, dried over sodium sulfate and concentrated. Chromatography of the crude product gave a mixture of sulfoxides. The mixture of the obtained sulfoxide, acetic anhydride (15 ml), tetrabutyl ammonium acetate (1.19g, 3.9 mmol) was then heated at 120° C. for 6 h 10 and the excess acetic anhydride was removed in vacuo. The residue was diluted with dichloromethane (200 ml), washed with water, brine, dried over sodium sulfate and concentrated. Chromatography of the crude product gave a mixture of acetate (0.601 g, 40%) as colourless oil: ¹H NMR in CDCl₃: δ1.10 (s, 9H), 2.05 (s, 1.2H), 2.10 (s, 1.8H), 3.60–4.50 (m, 4H), 5.30 (t, 0.4H, J=5.5 Hz), 5.58 (dd, 0.6H, J=6.5, 4.8Hz), 6.14–6.23 (m, 1H), 7.33–7.50 (m, 6H), 7.65–7.78 (m, 4H).

Example 29

2R-t-BUTYLDIPHENYLSILYLOXYMETHYL-4S-(N-4'-ACETYLCYTOSIN-1'-YL)-1,3-OXATHIOLANE AND 2R-t-BUTYLDIPHENYLSILYLOXY METHYL-4R-(N-4'-ACETYLCYTOSIN-1'-YL)-1,3-OXATHIOLANE

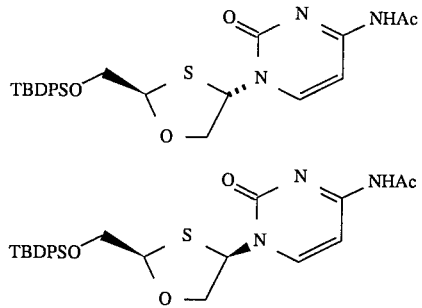

2,6-lutidine (0.054 ml, 0.49 mmol) and trimethylsilyl trifluoromethanesulfonate (0.095 ml, 0.49 mmol) were added to a suspension of N-4'-acetylcytosine (0.045 g, 0.29 mmol) in dichloroethane (2 ml) at room temperature under argon atomosphere. The mixture was stirred for 15 min and mixture of cis and trans 2R-t-butyldiphenylsiloxymethyl-4-acetoxy-1,3-oxathiolane (example 27) (0.100 g, 0.25 mmol) in dichloroethane (2 ml) and trimethylsilyl trifluoromethanesulfonate (0.048 ml, 0.25 mmol) were introduced successively. The reaction mixture was heated to reflux for half hour and diluted with dichloromethane, washed with saturated aqueous NaHCO₃ solution, water, brine, dried over sodium sulfate and concentrated. Chromatography of the crude product gave a mixture of trans and cis isomer which was subjected to preparative TLC seperation to give cis isomer (33 mg, 26%) [¹H NMR in CDCl₃: δ1.08 (s, 9H), 2.22 (s, 3H), 3.85–4.45 (m, 4H), 5.26 (t, 1H, J=4.3Hz), 6.54 (d, 1H, J=4.2Hz), 7.21 (d, 1H, J=7.4Hz), 7.35–7.50 (m, 6H), 7.60–7.75 (m, 4H), 8.23 (d, 1H, J=7.4Hz), 9.02 (bs,1H)] and trans isomer (49 mg, 39%) [¹H NMR in CDCl₃: δ1.04 (s, 9H), 2.21 (s, 3H), 3.56–4.26 (m, 4H), 5.64 (dd, 1H, J=6.8, 4.4Hz), 6.39 (d, 1H, J=3.6Hz), 7.31–7.48 (m, 7H), 7.58–7.71 (m, 4H), 8.01 (d, 1H, J=7.4Hz), 8.86 (bs, 1H)].

Example 30

2S-t-BUTYLDIPHENYLSILYLOXYMETHYL-4R-(N-4'-ACETYLCYTOSIN-1'-YL)-1,3-OXATHIOLANE AND 2S-t-BUTYLDIPHENYLSILYLOXY METHYL-4S-(N-4'-ACETYLCYTOSIN-1'-YL)-1,3-OXATHIOLANE

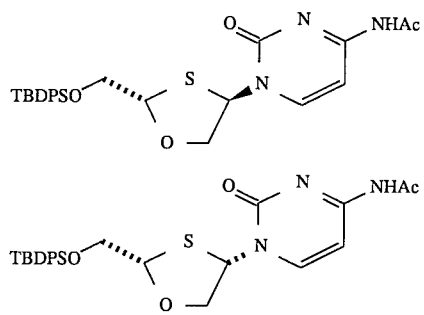

2,6-lutidine (0.131 ml, 1.13 mmol) and trimethylsilyl trifluoromethanesulfonate (0.218 ml, 1.13 mmol) were added to a suspension of N-4'-acetylcytosine (0.104 g, 0.68 mmol) in dichloroethane (2 ml) at room temperature under argon atmosphere. The mixture was stirred for 15 min and acetoxy-1,3-oxathiolane (example 28) (0.235 g 0.56 mmol) in dichloroethane (2 ml) and trimethylsilyl trifluoromethanesulfonate (0.109 ml, 1.13 mmol) were introduced successively. The reaction mixture was heated to reflux for half hour and diluted with dichloromethane, washed with saturated aqueous NaHCO₃ solution, water, brine, dried over sodium sulfate and concentrated. Chromatography (EtOAc) of the crude product gave a mixture of trans and cis isomer (0.225 g, 78%): ¹H NMR in CDCl₃: δ1.05 (s, 5.4H), 1.08 (s, 3.6H), 2.24 (s, 1.2H), 2.28 (s, 1.8H), 3.67–4.42 (m, 4H), 5.26 (t, 0.4H, J=4.3Hz ), 5.64 (dd, 0.6H, J=6.8, 4.3Hz), 6.40 (d, 0.6H, J=3.8Hz), 6.53 (d, 0.4H, J=4.1Hz), 7.20–7.75 (m, 11H), 8.00 (d, 0.6H, J=7.5Hz), 8.21 (d, 0.4H, J=7.5Hz), 9.63 (bs, 1H).

Example 31

2R-t-BUTYLDIPHENYLSILYLOXYMETHYL-4S-(N-4'-ACETYL-5'-FLUOROCYTOSIN-1'-YL)-1,3-OXATHIOLANE AND 2R-t-BUTYLDIPHENYLSILYLOXYMETHYL-4R-(N-4'-ACETYL-5'-FLUOROCYTOSIN-1'-YL)-1,3-OXATHIOLANE

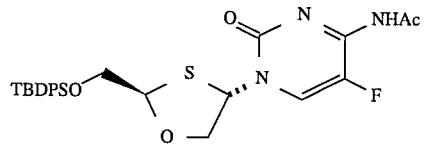

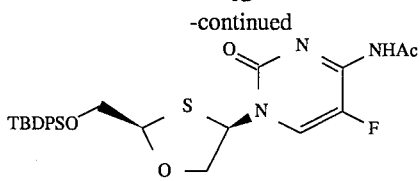

2,6-lutidine (0.124 ml, 1.07 mmol) and trimethylsilyl trifluoromethanesulfonate (0.207 ml, 1.07 mmol) were added to a suspension of N-4'-acetyl-5'-fluorocytosine (0.110 g, 0.64 mmol) in dichloroethane (3 ml) at room temperature under argon atomosphere. The mixture was stirred for 15 min and mixture of cis and trans 2R-t-butyldiphenylsiloxymethyl-4-acetoxy-1,3-oxathiolane (example 27) (0.223 g 0.54 mmol) in dichloroethane (3 ml) and trimethylsilyl trifluoromethane-sulfonate (0.103 ml, 0.54 mmol) were introduced successively. The reaction mixture was heated to reflux for half hour and diluted with dichloromethane, washed with saturated aqueous NaHCO₃ solution, water, brine, dried over sodium sulfate and concentrated. Chromotography of the crude product gave a mixture of trans and cis isomer which was subjected to preparative TLC separation to give cis isomer (97 mg, 34%) [$^1$H NMR in CDCl₃ δ1.08 (s, 9H), 2.65 (s, 3H), 3.90–4.50 (m, 4H), 5.27 (t, J=4.2Hz), 6.53 (d, 1H, J=4.2Hz), 7.32–7.530 (m, 6H), 7.55–7.76 (m, 4H), 8.21 (d, 1H, J=6.1Hz)] and trans isomer (68 mg, 24%) [$^1$H NMR in CDCl₃ δ1.07 (s, 9H), 2.63 (s, 3H), 3.56–4.26 (m, 4H), 5.68 (dd, J=6.9, 4.4Hz), 6.37 (d, 1H, J=2.4Hz), 7.30–7.53 (m, 6H), 7.57–7.75 (m, 4H), 7.93 (d, 1H, J=6.1Hz)].

Example 32

2S-t-BUTYLDIPHENYLSILYLOXYMETHYL-4R-(N-4'-ACETYL-5'-FLUOROCYTOSIN-1'-YL)-1,3-OXATHIOLANE AND 2S-t-BUTYLDIPHENYLSILYLOXYMETHYL-4S-(N-4'-ACETYL-5'-FLUOROCYTOSIN-1'-YL)-1,3-OXATHIOLANE

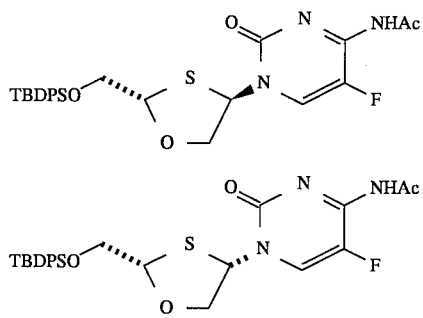

2,6-lutidine (0.248 ml, 2.13 mmol ) and trimethylsilyl trifluoromethanesulfonate (0.418 ml, 2.13 mmol) were added to a suspension of N-4'-acetyl-5'-fluorocytosine (0.218 g, 1.27 mmol) in dichloroethane (4.5 ml) at room temperature under argon atomosphere. The mixture was stirred for 15 min and mixture of cis and trans 2S-t-butyldiphenylsiloxymethyl-4-acetoxy-1,3-oxathiolane (example 28) (0.433g 1.06 mmol) in dichloroethane (4 ml) and trimethylsilyl trifluoromethane-sulfonate (0.206 ml, 1.06 mmol) were introduced successively. The reaction mixture was heated to reflux for half hour and diluted with dichloromethane, washed with saturated aqueous NaHCO₃ solution, water, brine, dried over sodium sulfate and concentrated. Chromotography of the crude product gave a mixture of trans and cis isomer which was subjected to preparative TLC separation to give cis isomer (145 mg, 26%) [$^1$H NMR in CDCl₃ δ1.09 (s, 9H), 2.66 (s, 3H), 3.90 –4.50 (m, 4H), 5.26 (t, J=4.1Hz), 6.53 (d, 1H, J=4.1Hz), 7.36–7.50 (m, 6H), 7.55–7.78 (m, 4H), 8.20 (d, 1H, J=6.1Hz)] and trans isomer (119 mg, 21%) [$^1$H NMR in CDCl₃ δ1.07 (s, 9H), 2.64 (s, 3H), 3.58–4.25 (m, 4H), 5.68 (dd, J=6.8, 4.2Hz), 6.37 (d, 1H, J=2.7Hz), 7.35–7.51 (m, 6H), 7.60–7.76 (m, 4H), 7.93 (d, 1H, J=6.1Hz)].

Example 33

2R-HYDROXYMETHYL-4R-(CYTOSIN-1'-YL)-1,3-OXATHIOLANE

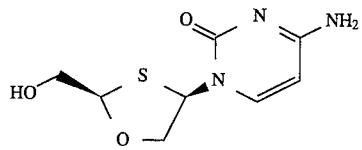

To a solution of 2R-t-butyldiphenylsiloxymethyl-4R-(N-4'-acetylcytosin-1'-yl)-1,3-oxathiolane (example 29) (72 mg, 0.14 mmol) in THF (3 ml) at ambient temperature under an argon atmosphere were slowly added tetrabutylammonium fluoride solution (0.212 ml, 1M in THF, 0.21 mmol) and glacial acetic acid (0.012 ml, 0.21 mmol). The reaction mixture was allowed to stir for 1 h, followed by the addition of silica gel (0.5 g). The resulting slurry was subjected to silical gel column chromatography (EtOAc-MeOH, 9:1) to give the desilylated product. The desilylated product was dissolved in saturated K₂CO₃ methanol solution and the reaction mixture was stirred at ambient temperature for half an hour. The reaction mixture was neutralized with 1N HCl/methanol solution followed by the addition of silica gel (0.5 g). The resulting slurry was subjected to silical gel column chromatography (EtOAc-MeOH, 4:1) to afford the product (27 mg, 91%) as white solid which was triturated in Et₂0MeOH: mp 200° C. (dec.); [α]$_D^{25}$ –126.8° (c, 0.5, MeOH); $^1$H NMR (DMSO-d₆): δ3.70–3.82 (m, 2H), 3.91 (dd, 1H, J=10.4, 4.6Hz), 4.38 (d, 1H, J=10.4Hz), 5.16 (t, 1H, J=4.6Hz), 5.32 (t, 1H, J=5.8Hz), 5.75 (d, 1H, J=7.4Hz), 6.32 (d, 1H, J=4.6Hz), 7.12 (bs, 1H), 7.23 (bs, 1H), 7.84 (d, 1H, J=7.4Hz); $^{13}$C NMR (DMSO-d₆): δ62.7, 63.1, 77.4, 89.0, 95.6, 142.4, 155.4, 165.8.

Example 34

2S-HYDROXYMETHYL-4S-(CYTOSIN-1'-YL)-1,3-OXATHIOLANE

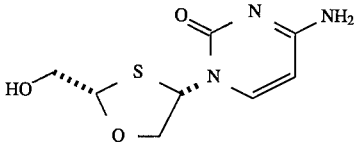

To a solution of 2S-t-butyldiphenylsiloxymethyl-4S-(N-4'-acetylcytosin-1'-yl)-1,3-oxathiolane (example 30) (202 mg, 0.40 mmol) in THF (3.5 ml) at ambient temperature under an argon atomsphere were slowly added tetrabutylammonium fluoride solution (0.595 ml, 1M in THF, 0.60 mmol) and glacial acetic acid (0.034 ml, 0.60 mmol). The reaction mixture was allowed to stir for 1 h, followed by the addition of silica gel (0.9 g). The resulting slurry was subjected to silical gel column chromatography (EtOAc- MeOH, 9:1) to give the desilylated product. The desilylated product was dissolved in saturated $K_2CO_3$ methanol solution and the reaction mixture was stirred at ambient temperature for half an hour. The reaction mixture was neutralized with 1N HCl methanol solution followed by the addition of silica gel (0.9 g). The resulting slurry was subjected to silical gel column chromatography (EtOAc-MeOH, 4:1) to afford the product (74 mg, 81%) as white solid which was triturated in $Et_2O$-MeOH: mp 220° C. (dec.); $[\alpha]_D^{25}$ +118.6° (c, 0.5, MeOH); $^1$H NMR (DMSO-$d_6$): δ3.70–3.82 (m, 2H), 3.92 (dd, 1H, J=10.6, 5.32 (t, 1H, J=5.8Hz), 5.75 (d, 1H, J=7.4Hz), 6.32 (d,1H, J=4.6Hz), 7.12 (bs, 1H), 7.22 (bs, 1H), 7.85 (d, 1H, J=7.4Hz); $^{13}$C NMR (DHSO-$d_6$): δ63.0, 63.1, 77.4, 88.9, 95.1, 142.4, 155.4, 165.7.

Example 35

2R -HYDROXYMETHYL-4S -(CYTOSIN-1'-YL)-1,3-OXATHIOLANE

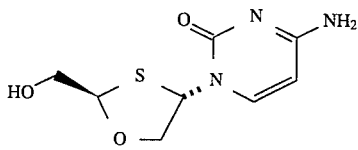

To a solution of 2R-t-butyldiphenylsiloxymethyl-4S-(N-4'-acetylcytosin-1'-yl)-1,3-oxathiolane (example 29)(90 mg, 0.18 mmol) in THF (3 ml) at ambient temperature under an argon atomsphere were slowly added tetrabutylammonium fluoride solution (0.265 ml, 1M in THF, 0.26 mmol) and glacial acetic acid (0.015 ml, 0.26 mmol). The reaction mixture was allowed to stir for 1 h, followed by the addition of silica gel (0.5 g). The resulting slurry was subjected to silical gel column chromatography (EtOAc-MeOH, 9:1) to give the desilylated product. The desilylated product was dissolved in saturated $K_2CO_3$ methanol solution and the reaction mixture was stirred at ambient temperature for half an hour. The reaction mixture was neutralized with 1N HCl methanol solution followed by the addition of silica gel (0.5 g). The resulting slurry was subjected to silical gel column chromatography (EtOAc-MeOH, 4:1) to afford the product (33 mg, 81%) as white solid which was triturated in $Et_2O$-MeOH: mp 146°–148° C. (dec.); $[\alpha]_D^{25}$ +190.2° (c, 0.62, MeOH); $^1$H NMR (DMSO-$d_6$): δ3.53–3.65 (m, 1H), 4.10–4.28 (m, 2H), 5.22 (t, 1H, J=5.5Hz), 5.55 (dd, 1H, J=7.4, 4.6Hz), 5.75 (d, 1H, J=7.4Hz), 6.28 (d, 1H, J=3.8Hz), 7.13 (bs, 1H), 7.20 (bs, 1H), 7.65 (d, 1H, J=7.5Hz); $^{13}$C NMR (DMSO-$d_6$): δ63.0, 63.6, 74.7, 87.6, 95.2, 142.3, 155.4, 165.7.

Example 36

2S-HYDROXYMETHYL-4R-(CYTOSIN-1'-YL)-1,3-OXATHIOLANE

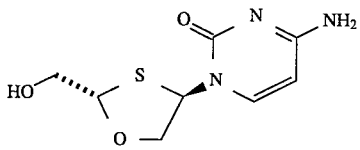

To a solution of 2S-t-butyldiphenylsiloxymethyl-4R-(N-4'-acetylcytosin-1'-yl)-1,3-oxathiolane (example 30) (245 mg, 0.48 mmol) in THF (4 ml) at ambient temperature under an argon atmosphere were slowly added tetrabutylammonium fluoride solution (0.722 ml, 1M in THF, 0.72 mmol) and glacial acetic acid (0.025 ml, 0.43 mmol). The reaction mixture was allowed to stir for 1 h, followed by the addition of silica gel (0.9 g). The resulting slurry was subjected to silical gel column chromatography (EtOAc-MeOH, 9:1) to give the desilylated product. The desilylated product was dissolved in saturated $K_2CO_3$ methanol solution and the reaction mixture was stirred at ambient temperature for half an hour. The reaction mixture was neutralized with 1N HCl methanol solution followed by the addition of silica gel (0.9 g). The resulting slurry was subjected to silical gel column chromatography (EtOAc-MeOH, 4:1) to afford the product (92 mg, 83%) as white solid which was triturated in $Et_2O$-MeOH: mp 152°–154° C. (dec.); $[\alpha]_D^{25}$ –195.4° (c, 0.79, MeOH); $^1$H NMR (DMSO-$d_6$): δ3.53–3.65 (m, 1H), 4.10–4.28 (m, 2H), 5.22 (t, 1H, J=S.7Hz), 5.55 (dd, 1H, J=7.4, 4.5Hz), 5.75 (d, 1H, J=7.4Hz), 6.29 (d, 1H, J=4.0Hz), 7.14 (bs, 1H), 7.21 (bs, 1H), 7.65 (d, 1H, J=7.4Hz); $^{13}$C NMR (DMSO-$d_6$): δ63.0, 63.6, 74.7, 87.6, 95.1, 142.2, 155.5, 165.7.

Example 37

2R-HYDROXYMETHYL-4R-(5'-FLUOROCYTOSIN-1'-YL)-1,3-OXATHIOLANE
(BCH-1530)

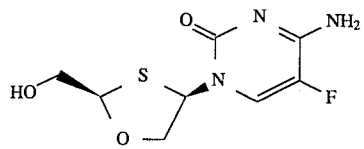

To a solution of 2R-t-butyldiphenylsiloxymethyl-4R-(N-4'-acetyl-5'-fluorocytosin-1'-yl)-1,3-oxathiolane (example 31) (152 mg, 0.29 mmol) in THF (3.5 ml) at ambient temperature under an argon atmosphere were slowly added tetrabutylammonium fluoride solution (0.432 ml, 1M 0 in THF, 0.43 mmol) and glacial acetic acid (0.025 ml, 0.43 mmol). The reaction mixture was allowed to stir for 1 h, followed by the addition of silica gel (0.5 g). The resulting slurry was subjected to silical gel column chromatography (EtOAc-MeOH, 9:1) to give the desilylated product. The desilylated product was dissolved in saturated $K_2CO_3$ methanol solution and the reaction mixture was stirred at ambient temperature for half an hour. The reaction mixture was neutralized with 1N HCl methanol solution followed by the addition of silica gel (0.5 g). The resulting slurry was subjected to silical gel column chromatography (EtOAc-MeOH, 4:1) to afford the product (58 mg, 81%) as white solid which was triturated in $Et_2O$-MeOH: mp 183° C. (dec.); $[\alpha]_D^{25}$ –86.5° (c, 0.57, MeOH); 1H NMR (DMSO-$d_6$): δ3.70–4.50 (m, 4H), 5.18 (t, 1H, J=3.6Hz), 5.44 (t, 1H, J=5.8Hz), 6.25–6.30 (m, 1H), 7.56 (bs, 1H), 7.80 (bs, 1H), 8.14 (d, 1H, J=7.2Hz); $^{13}$C NMR (DMSO-$d_6$): δ62.2, 63.4, 77.5, 88.9, 126.7, 127.1, 134.7, 137.9, 153.8, 157.5, 157.7.

Example 38

2S-HYDROXYMETHYL-4S-(5'-FLUOROCYTOSIN-1'-YL)-1,3-OXATHIOLANE (BCH-1529)

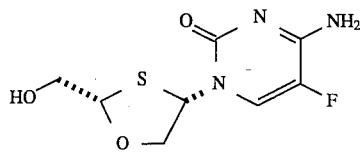

To a solution of 2S-t-butyldiphenylsiloxymethyl-4S-(N-4'-acetyl-5'-fluorocytosin-1'-yl)-1,3-oxathiolane (example 32) (78 mg, 0.15 mmol) in THF (3 ml) at ambient temperature under an argon atmosphere were slowly added tetrabutylammonium fluoride solution (0.222 ml, 1M in THF, 0.22 mmol) and glacial acetic acid (0.013 ml, 0.22 mmol). The reaction mixture was allowed to stir for 1 h, followed by the addition of silica gel (0.5 g). The resulting slurry was subjected to silical gel column chromatography (EtOAc-MeOH, 9:1) to give the desilylated product. The desilylated product was dissolved in saturated $K_2CO_3$ methanol solution and the reaction mixture was stirred at ambient temperature for half hour. The reaction mixture was neutralized with 1N HCl methanol solution followed by the addition of silica gel (0.5 g). The resulting slurry was subjected to silical gel column chromatography (EtOAc-MeOH, 4:1) to afford the product (36 mg, 98%) as white solid which was triturated in $Et_2O$-MeOH: mp 180° C. (dec.); $[\alpha]_D^{25}$ +75.7° (c, 0.56, MeOH); $^1$H NMR (DMSO-$d_6$): δ3.69–4.50 (m, 4H), 5.18 (t, 1H, J=3.7Hz), 5.44 (t, 1H, J=5.8Hz), 6.25–6.29 (m, 1H), 7.55 (bs, 1H), 7.8 (bs, 1H), 8.14 (d, 1H, J=7.2Hz); $^{13}$C NMR (DMSO-$d_6$): 61.8, 63.1, 77.1, 88.6, 126.3, 126.8, 134.4, 137.6, 153.5, 157.1, 157.3.

Example 39

2R-HYDROXYMETHYL-4S-(5'-FLUOROCYTOSIN-1'-YL)-1,3-OXATHIOLANE

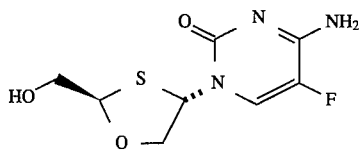

To a solution of 2R-t-butyldiphenylsiloxymethyl-4S-(N-4'-acetyl-5'-fluorocytosin-1'-yl)-1,3-oxathiolane (example 31) (90.5 mg, 0.17 mmol) in THF (3 ml) at ambient temperature under an argon atmosphere were slowly added tetrabutylammonium fluoride solution (0.257 ml, 1M in THF, 0.26 mmol) and glacial acetic acid (0.015 ml, 0.26 mmol). The reaction mixture was allowed to stir for 1 h, followed by the addition of silica gel (0.5 g). The resulting slurry was subjected to silical gel column chromatography (EtOAc-MeOH, 9:1) to give the desilylated product. The desilylated product was dissolved in saturated $K_2CO_3$ methanol solution and the reaction mixture was stirred at ambient temperature for half an hour. The reaction mixture was neutralized with 1N HCl methanol solution followed by the addition of silica gel (0.5 g). The resulting slurry was subjected to silical gel column chromatography (EtOAc-MeOH, 4:1) to afford the product (38 mg, 89%) as white solid which was triturated in $Et_2O$-MeOH: mp 183° C. (dec.); $[\alpha]_D^{25}$ +171° (c, 0.09, MeOH); $^1$H NMR (DMSO-$d_6$): δ3.52–3.65 (m, 1H), 4.09–4.30 (m, 2H), 5.34 (t, 1H, J=6.2Hz), 5.64 (dd, 1H, J=7.3, 4.3Hz), 6.22–6.25 (m, 1H), 7.57 (bs, 1H), 7.81 (d, 1H, J=7.1Hz); $^{13}$C NMR (DMSO-$d_6$): 63.6, 74.5, 87.6, 126.3, 126.7, 134.9, 138.1, 153.8, 157.6, 157.8.

Example 40

2S-HYDROXYMETHYL-4R-(5'-FLUOROCYTOSIN-1'-YL)-1,3-OXATHIOLANE (BCH-1528)

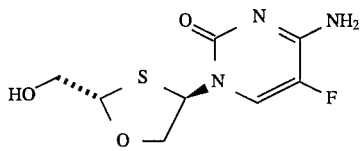

To a solution of 2S-t-butyldiphenylsiloxymethyl-4R-(N-4'-acetyl-5'-fluorocytosin-1'-yl)-1,3-oxathiolane (example 32) (65.8 mg, 0.125 mmol) in THF (3 ml) at ambient temperature under an argon atomsphere were slowly added tetrabutylammonium fluoride solution (0.187 ml, 1M in THF, 0.187 mmol) and glacial acetic acid (0.011 ml, 0.187 mmol). The reaction mixture was allowed to stir for 1 h, followed by the addition of silica gel (0.5 g). The resulting slurry was subjected to silica gel column chromatography (EtOAc-MeOH, 9:1) to give the desilylated product. The desilylated product was dissolved in saturated $K_2CO_3$ methanol solution and the reaction mixture was stirred at ambient temperature for half hour. The reaction mixture was neutralized with 1N HCl methanol solution followed by the addition of silica gel (0.5 g). The resulting slurry was subjected to silica gel column chromatography (EtOAc-MeOH, 4:1) to afford the product (28 mg, 91%) as white solid which was triturated in $Et_2O$-MeOH: mp 180° C. (dec.); $[\alpha]_D^{25}$ −179° (c, 0.31, MeOH); $^1$H NMR (DMSO-$d_6$): δ3.51–3.62 (m, 1H), 4.10–4.30 (m, 2H), 5.22 (t, 1H, J=5.3Hz), 5.62 (dd, 1H, J=6.9, 4.0Hz), 6.22–6.25 (m, 1H), 7.56 (bs, 1H), 7.8 (d, 1H, J=7.1Hz); $^{13}$C NMR (DMSO-$d_6$): δ63.4, 77.5, 88.9, 126.7, 127.1, 134.7, 137.9, 153.8, 157.4, 158.0.

Example 41

CIS AND TRANS 2-p-NITROBENZOYLOXYMETHYL-4-p-NITROBENZOYLOXY-1,3-DITHIOLANE

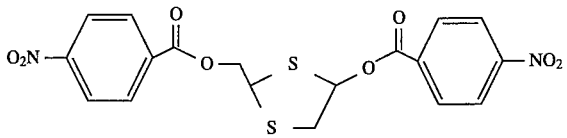

A solution of diisobutylaluminium hydride (1.5M in toluene) (62.67 mL, 94.02 mmol) was added to a solution of 2-benzoyloxymethyl-4-oxo-1,3-dithiolane (Satsumahyashi et al., J. Org. Chem. 38, 3953–3954 (1973)) (7.69 g, 31.34 mmol) in toluene (400 mL) at −78° C. After 1 h the reaction was quenched with water, the resulting thick mixture was then filtered to remove aluminium salts. The filtrate was extracted with ethyl acetate (3X), the combined organic extracts were washed with brine, dried and concentrated to give a yellow oil. The oil was purified by flash chromatography (25% EtOAc/Hexanes) to give a mixture of cis and trans 2-hydroxymethyl-4-hydroxy-1,3-dithiolane as a colourless oil, 1.72g (40%). $^1$H NMR (CDCl$_3$) (300 MHz) δ: 5.80+5.75 (dm's, 1H, 8Hz, C4—H̲), 4.87 (t, 1H, 3Hz, OH̲), 4.53+4.32 (dd, 1H, 6Hz, 1Hz, C2—H̲), 3.78 (m, 1H, CH̲$_2$OH), 3.53 (m, 1H, CH̲$_2$OH), 3.44+3.27 (dd's, 1H, 12Hz, 2Hz, C5-H̲), 3.37+3.14 (dd's, 1H, 12Hz, 3Hz, C5—H̲), 2.88 (m, 1H, OH̲).

p-Nitrobenzoyl chloride (4.72 g, 25.42 mmol) was added to a solution of cis and trans-2-hydroxymethyl-4-hydroxy-1,3-dithiolane (1.38 g, 9.08 mmol) in dry pyridine (50 mL) at 0° C. the reaction mixture was then placed in the refrigerator for 18 h. The reaction mixture was then poured into water and extracted with methylene chloride (3X). The combined organic extracts were washed with water, brine, dried and concentrated to give a yellow solid, 3.68 g (90%). $^1$H NMR (CDCl$_3$) (300 MHz) δ: (8.27 (m, 8H, Ar-H̲), 6.86+6.81 (dd's, 1H, 3Hz, 2Hz, C4-H̲), 4.96+4.87 (t's, 1H, 7Hz, C2—H̲), 4.47 (m, 2H, CH̲$_2$OAr), 3.5 (m, 2H, C5—H̲).

Example 42

CIS AND TRANS-2-p-NITROBENZOYLOXYMETHYL-4-(5'-FLUOROCYTOSIN-1'-YL)-1,3-DITHIOLANE

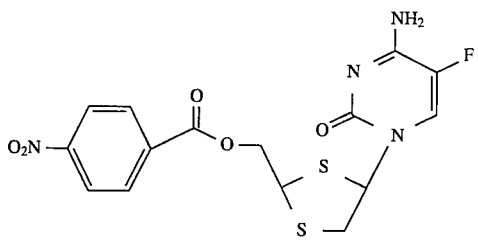

A mixture of 5-fluorocytosine (0.72 g, 5.52 mmol) and ammonium sulfate (50 µg) in HMDS (100 mL) was heated to reflux for 18 h. Solvent was removed in vacuo and the resulting white solid was left on the vacuum pump for 1 h. A solution of the silylated 5-fluorocytosine in acetonitrile (20 mL) was added by cannula to a solution of cis and trans-2-p-nitrobenzoyloxymethyl-4-p-nitrobenzoyloxy-1,3-dithiolane (example 41) (1.00 g, 2.22 mmol) in acetonitrile (60 mL). This was followed by the addition of trimethylsilyl-trifluoromethanesulfonate (0.99 g., 4.44 mmol), and the solution was stirred at room temperature for 18 h. The reaction mixture was poured into a saturated sodium bicarbonate solution and the aqueous phase was extracted with dichloromethane (3X). The combined organic extracts were dried and concentrated to give a yellow oil. The oil was purified by flash chromatography (5% methanol:methylene chloride) to give the title compounds as a white solid 0.060 g (7%), (1:1) cis and trans. $^1$H NMR (CDCl$_3$) (300 MHz) δ: 8.33 (d, 2H, 7Hz), 8.27 (s, 1H), 8.20 (d, 2H, 7Hz), [6.78 (d, 0.5H, 3Hz), 6.70 (t, 0.5H, 4Hz)] anomeric, 5.98 (br n, 2H), 5.00+4.96 (t's, 1H, 4Hz), [4.78 (m, 1H), 4.50 (dd, 0.5H, 7Hz, 3Hz), 4.38 (dd, 0.5H, 4Hz)], 3.55 (m, 1H), 3.42 (d, 1H, 13Hz).

Example 44

CIS-2-HYDROXYMETHYL-4-(5'-FLUOROCYTOSIN-1'-YL)-1,3 DITHIOLANE AND TRANS-2-HYDROXYMETHYL-4-(5'-FLUOROCYTOSIN-1'-YL)-1,3-DITHIOLANE

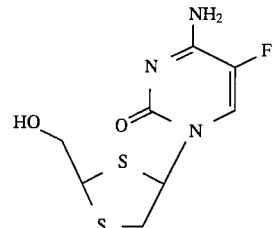

CIS
(BCH 1026)

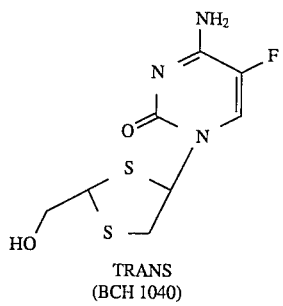

TRANS
(BCH 1040)

Ammomia gas was bubbled into a solution of cis and trans-2-nitrobenzoyloxymethyl -4-(5'-fluorocytosin-1'-yl)-1,3-dithiolane (example 41) (0.060 g, 0.145 mmol) in methanol (20 mL) at 0° C. for 15 min. The mixture was then stirred for 18 h. The solvent was removed in vacuo to give a white solid. The solid was first purified by flash chromatography (ethyl acetate) and also by preparative HPLC to give the title compound, cis isomer, 0.004 g (10%). $^1$H NMR (DMSO) (300MHz) δ: 8.34 (d, 1H, 7.5Hz), 7.83 (brs, H), 7.59 (brs, 1H), 6.39 (m, 1H), 5.57 (t, 1H, 5.5Hz), 4.62 (t, 1H, 6Hz), 3.74 (t, 2H, 6Hz), 3.59 (m, 2H). And the trans isomer, 0.0073 g (20%), $^1$H NMR (DMSO) (300MHz) 6:8.10 (d, 1H, 7Hz), 7.78 (brs, H), 7.54 (brs, 1H), 6.41 (t, 1H, 2Hz), 5.36 (t, 1H, 5.5Hz), 4.81 (t, 1H, 7Hz), 3.45 (m, 4H).

Example 45

ANTIVIRAL ACTIVITY: FORMAZAN ASSAY ON MT-4 AND 3TC™-RESISTANT CELL LINES

Anti-HIV-1 antiviral activity was determined in MT-4 cells and MT-4 cells that have been made resistant to 3TC™. A suspension of cells (approximately 10$^6$ cells/ml) in RPMI 1640 growth medium was infected with HIV-1 strain RF at a M.O.I. of 10$^{-3}$ infectious units/cell. An uninfected cell suspension was prepared in parallel to evaluate drug-induced cytotoxicity. The two suspensions were incubated for 90 minutes at room temperature. Test compounds were serially diluted in 10-fold decrements from 100 µg/ml to 0.01 µg/ml (final concentrations in two 96 well microtitre plates. 20 µl of infected cell suspension were inoculated into each well of one of the plates (antiviral), while 20 µl of uninfected cell suspension were added to each well of the second plate (cytotoxicity). The plates were then incubated for 7 days at 37° C. After incubation, 10 µl of 3-(4,5-dimethylthiazol-2-yl)-2,5-diphenyltetrazolium bromide (MTT) at 20 mg/ml was added to all wells and the plates incubated for a further 90 minutes at 37° C.

150 µl of 10% (v/v) alcoholic Triton X-100 was then added and the cells resuspended. After 15 minutes at room temperature, the plates were analyzed in a Multiskan MC reader at 405 nm. Conversion of yellow MMT to its formazan derivative is maximum in uninfected cells, and absent in untreated infected cells. The optical density values for the cytotoxicity controls and the antiviral test wells were graphically plotted and the dose of compounds required to inhibit the conversion of MMT to 50% of the untreated uninfected controls was calculated. In this way, both the 50% cytotoxic dose (CD 50%) and the 50% anti-viral dose (ID 50%) can be calculated. Table 1 shows CD 50% and ID 50% values obtained for:

TABLE 1

(MT-4 assay)

| COMPOUND | $ID_{50}$ (µg/ml) | $CD_{50}$ (µg/ml) |
| --- | --- | --- |
| Experiment 1 | | |
| BCH - 270 (example 7) | 4.0 | >100 |
| BCH - 1512 (example 33) | 13 | >100 |
| BCH - 1533 (example 34) | 4.4 | >100 |
| BCH - 1529 (example 38) | 2.9 | 100 |
| BCH - 1530 (example 37) | 6.0 | >100 |
| AZT (reference) | 0.01 | >1 |
| Experiment 2 | | |
| BCH - 1081 (example 20) | 2.5 | >100 |
| BCH - 1026 (example 42) | 4.8 | >100 |
| AZT (reference) | 0.003 | >1 |
| Experiment 3 | | |
| BCH - 373 (example 17) | 9.3 | >100 |
| AZT (reference) | 0.0004 | >1 |

TABLE 2

3TC-RESISTANT CELLS (Met[184] → Ile mutation)

| COMPOUND | $ID_{50}$ (µg/ml) | $CD_{50}$ (µg/ml) |
| --- | --- | --- |
| BCH - 1512 (example 33) | 8.5 | >100 |
| BCH - 1533 (example 34) | 42 | >100 |
| BCH - 1529 (example 38) | 3.0 | 100 |
| BCH - 1530 (example 37) | 3.4 | >100 |
| 3TC ™ | >100 | >100 |

INHIBITION OF SYNCYTIUM FORMATION

C8166 cells were infected with HIV-1 (strain RF) at a mol of $1 \times 10^{-3}$ infectious units/cell and adsorbed at room temperature for 60 minutes. After adsorption, the cells were washed three times in growth medium. Aliquots of $10^5$ cells were added to each well of 24-well plates containing serial dilutions of test compounds at final concentrations of 50 µg/ml to 0.05 µg/ml in RPMI® 1640 growth medium. Untreated infected cells and untreated uninfected cells were also included as controls. The plates were incubated at 37° C./5% $CO_2$ for 3–4 days in humidified containers. The cells were examined daily for evidence of HIV-1 induced syncytium formation. The syncytia were quantified by reference to the untreated infected controls, and the dose of compound required to reduce the cytopathic effect by 50% ($ID_{50}$) was calculated.

TABLE 3

(SYNCYTIUM FORMATION)

| COMPOUND | $ID_{50}$ (µg/ml) | $CD_{50}$ (µg/ml) |
| --- | --- | --- |
| BCH - 1529 (example 38) | 0.03 | >100 |
| BCH - 1530 (example 37) | 0.17 | >100 |
| BCH - 1533 (example 34) | 0.08 | >100 |

CBL ASSAY

Assays on cord blood lymphocytes were done substantially as described in Gu et al., J. Virol. (1992), 66:7128–7135.

In short, viruses (HTLV-III$_B$) that had initially been grown on MT-4 cells were passaged onto phytohemaglutinin-prestimulated cord blood lymphocytes (CBL). For subsequent analysis, samples of CBL ($5 \times 10^5$ cells per mL) were pretreated with various concentrations of the different compounds for 4 h and were then inoculated with CBL-grown HIV-1 at a multiplicity of infection of 1.0 in the concentration of the compound used for the pretreatment. Fresh medium, including the appropriate concentration of the compound was added three times weekly, and fresh phytohemaglutinin-prestimulated CBL ($5 \times 10^5$ cells per mL) were added at 2-day intervals. The calculation of $IC_{50}$ was determined on the basis of RT levels in culture fluids as described in Gao et al., (1992), J. Virol. 66: 12–19.

TABLE 4

(CBL)

| COMPOUND | $ID_{50}$ (µg/ml) | $CD_{50}$ (µg/ml) |
| --- | --- | --- |
| BCH -270 (example 7) | 0.03 | >23 |
| BCH - 1512 (example 33) | 0.05–1.22 | >23 |
| BCH - 1533 (example 34) | 0.03–1.22 | >23 |
| BCH - 1530 (example 37) | 0.02–0.05 | >23 |
| BCH - 1529 (example 38) | 0.002–0.005 | >23 |
| AZT (reference) | <0.002 | >1 |

DETERMINATION OF IC50 (µM) IN HIV-1 ACUTELY INFECTED CELL LINES IN THE PRESENCE OF DIFFERENT ANTIVIRAL COMPOUNDS

Various cell lines were infected with HTLV-IIIb (TCID50=200) and then cultured with various concentrations of drug. IC50 was determined by measuring p24 antigen levels in the supernatant of cultures at day 6 of infection.

TABLE 5

| | $ID_{50}$ (µg/ml) | | | | |
| --- | --- | --- | --- | --- | --- |
| COMPOUND | MT-4 | Jurkat | H9 | U937 | CEM |
| BCH - 1512 (example 33) | 2.8 | 3.0 | 0.3 | 0.4 | 0.2 |
| BCH - 1529 (example 38) | 3.0 | 3.5 | 0.1 | 0.6 | 0.2 |
| BCH - 1530 (example 37) | 3.2 | 6.0 | 1.0 | 0.4 | 0.3 |
| BCH - 1533 (example 34) | 0.9 | 1.8 | 0.075 | 0.3 | 0.4 |
| AZT (reference) | 0.03 | >10 | 0.07 | >10 | >10 |

EVALUATION OF CELL CULTURE INHIBITORY DOSE (CCID50)

Cell growth was determined by cell counting and viability by trypan blue exclusion 7 days post drug treatment.

CCID50 is expressed as the drug concentration which inhibits 50% of cell growth.

TABLE 6

| | (CCID50 in Different Cells (µM)) | | | | | |
|---|---|---|---|---|---|---|
| COMPOUNDS | CMBCs | MT-4 | U937 | Jurkat | H9 | CEM |
| BCH - 1512 | >500 | >500 | >500 | 450 | >500 | >500 |
| BCH - 1529 | >500 | >500 | >500 | >500 | >500 | >500 |
| BCH - 1530 | >500 | >500 | >500 | >500 | >500 | >500 |
| BCH - 1533 | 105 | >500 | 22 | 11 | >500 | 103 |
| AZT | 45 | 110 | 110 | >500 | 200 | 500 |

INHIBITION OF HUMAN HEPATITIS B VIRUS

The method used for this test is described in detail in Korba et al., Antiviral Research 15, 217–228 (1992) which is shortly described as follows: Hep G2 cells transfected with human hepatitis B virus genomic DNA (2.2.15 cells) were grown and maintained in RPMI-1640 culture medium containing %5 foetal bovine serum, 2 mM glutamine and 50 µg/ml gentamicin sulphate, and checked routinely for G418 resistance. Cultures of 2.2.15 cells were grown to confluence in 24 well tissue culture plates and maintained for 2 to 3 days in that condition prior to drug treatment.

Drugs were dissolved in sterile water or sterile 50% DMSO in water at concentrations 100-fold higher than the higher test concentration. These solutions were diluted as needed in culture medium.

The culture medium on the confluent cells was changed 24 hours prior to exposure to test compounds. During the 10 day treatment, the culture medium was changed daily. After 10 days of the treatment, the culture medium was collected and frozen at −70° C. for HBV DNA analysis.

To analyse extracellular HBV DNA, 0.2 ml samples of culture medium were incubated for 20 minutes at 25° C. in 1M NaOH/10X SSC (IX SSC is 0.15M NaCl/0.015M Sodium Citrate, pH 7.2) and then applied to nitrocellulose membranes presoaked in 20X SSC. Filters were then rinsed in 2X SSC and baked at 80° C. for 1 hour under vacuum.

A purified 3.2 kb EcoR1 HBV DNA fragment was labelled with [$^{32}$P]dCTP by nick translation and used as a probe to detect HBV DNA on the dot-blot by DNA hybridisation. After washing, the hybridised blot was dried and $^{32}$P was quantified using an Ambis beta scanner.

TABLE 7

| | (HBV) | |
|---|---|---|
| COMPOUND | ID$_{50}$ (µg/ml) | CD$_{50}$ (µg/ml) |
| BCH - 270 (example 7) | 7.5 | >10 |
| BCH - 1533 (example 33) | 4 | >10 |

We claim:

1. A compound of formula (I) or a pharmaceutically acceptable salt or ester of that compound, the geometric and optical isomers thereof, and mixtures of those isomers:

wherein:

X is selected from the group consisting of S, S=O, SO$_2$;

Y is O;

R$_1$ is hydrogen; and

R$_2$ is selected from the group consisting of:

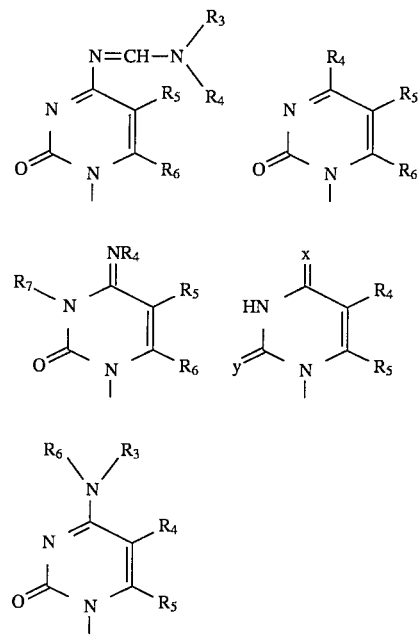

wherein:

x and y are independently O or S;

R$_3$ is selected from the group consisting of hydrogen, C$_{1-10}$ acyl, hydroxyl, amino, C$_{1-6}$ alkyl, alkenyl or alkynyl, and carboxyl;

R$_4$, R$_5$ and R$_6$ are independently selected from the group consisting of hydrogen, hydroxymethyl; trifluoromethyl, C$_{1-6}$ alkyl, alkenyl or alkynyl, bromine, chlorine, fluorine, iodine, hydroxyl, amino, cyano, carboxyl, carbamoyl, alkoxycarbonyl, arylthio, acyloxy, thiocarboxy, thiocarbamoyl, carbamate, ureido, amidino, aryloxy and carboxamide; and R$_7$ is selected from the group consisting of hydrogen, bromine, chlorine, fluorine, iodine, amino, hydroxyl, C$_{1-10}$ acyl, C$_{1-10}$ alkyl, and C$_{7-20}$ aralkyl.

2. The compound of formula (I) according to claim 1 wherein R$_2$ is selected from the group consisting of:

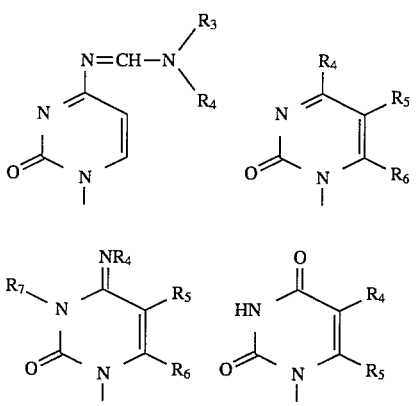

-continued

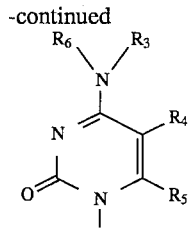

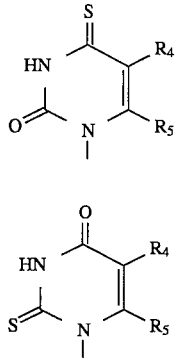

wherein:

R₃ is selected from the group consisting of hydrogen, C₁₋₁₀ acyl, hydroxyl, C₁₋₆ alkyl, C₂₋₆ alkenyl or alkynyl;

R₄ and R₅ are independently selected from the group consisting of hydrogen, hydroxymethyl, trifluoromethyl, C₁₋₆ alkyl, C₂₋₆ alkenyl or alkynyl, bromine, chlorine, fluorine, iodine, and arylthio;

R₆ is selected from the group consisting of hydrogen, bromine, chlorine, fluorine, iodine, cyano, carboxyl, carboxamide, ethoxycarbonyl, carbamoyl, and thiocarbamoyl; and R₇ is selected from the group consisting of hydrogen, bromine, chlorine, fluorine, iodine, amino, and hydroxyl.

3. The compound according to claim 5 wherein R₂ is

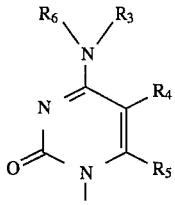

wherein:

R₃ is selected from the group consisting of hydrogen, C₁₋₁₀ acyl, hydroxyl, C₁₋₆ alkyl, C₂₋₆ alkenyl or alkynyl;

R₄ and R₅ are independently selected from the group consisting of hydrogen, hydroxymethyl, trifluoromethyl, C₁₋₆ alkyl, C₂₋₆ alkenyl or alkynyl, bromine, chlorine, fluorine, iodine, and arylthio; and R₆ is selected from the group consisting of hydrogen, bromine, chlorine, fluorine, iodine, cyano, carboxyl, carboxamide, ethoxycarbonyl, carbamoyl, and thiocarbamoyl.

4. The compound according to any one of claims 1 and 2–3 in the form of its cis isomer.

5. A compound of formula (Ia), or a pharmaceutically acceptable salt or ester thereof, the geometric and optical isomers thereof, and mixtures of those isomers:

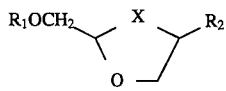

wherein:

X is selected from the group consisting of S, S=O, and SO₂;

R₁ is hydrogen; and

R₂ is selected from the group consisting of

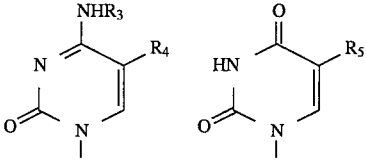

wherein:

R₃ is selected from the group consisting of hydrogen, C₁₋₁₀ acyl, hydroxyl, C₁₋₆ alkyl, C₂₋₆ alkenyl or alkynyl; and R₄ and R₅ are independently selected from the group consisting of hydrogen, hydroxymethyl, trifluoromethyl, C₁₋₆ alkyl, C₂₋₆ alkenyl or alkynyl, bromine, chlorine, fluorine, iodine, and arylthio.

6. A compound according to claim 5, wherein R₂ is:

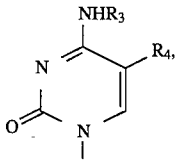

R₃ is hydrogen and R₄ is hydrogen or fluorine.

7. The compound of formula (I) according to claim 1 wherein at least one of R₄, R₅ and R₆ is ethoxycarbonyl.

8. The compound of formula (I) according to claim 15 wherein at least one of R₄, R₅ and R₆ is ethoxycarbonyl.

9. The compound according to claim 1 selected from the group consisting of:

cis-2-hydroxymethyl-4-(cytosin-1'-yl)-1,3-oxathiolane (BCH-270), trans-2-hydroxymethyl-4-(cytosin-1'-yl)-1,3-oxathiolane, and mixtures thereof;

cis-2-hydroxymethyl-4-(uracil-1'-yl)-1,3-oxathiolane, trans-2-hydroxymethyl-4-(uracil-1'-yl)-1,3-oxathiolane, and mixtures thereof;

cis-2-hydroxymethyl-4-(thymin-1'-yl)-1,3-oxathiolane, trans-2-hydroxymethyl-4-(thymin-1'-yl)-1,3-oxathiolane, and mixtures thereof;

cis-2-hydroxymethyl-4-(5'-fluorocytosin-1'-yl)-1,3-oxathiolane (BCH-1081);

2R-hydroxymethyl-4R-(cytosin-1'-yl)-1,3-oxathiolane (BCH-1512), 2S-hydroxymethyl-4S-(cytosin-1'-yl)-1,3-oxathiolane (BCH-1533), 2R-hydroxymethyl-4S-(cytosin-1'-yl)-1,3-oxathiolane (BCH-1511), 2S-hydroxymethyl-4R-(cytosin-1'-yl)-1,3-oxathiolane (BCH-1532), and mixtures thereof;

2R-hydroxymethyl-4R-(5'-fluorocytosin-1'-yl)-1,3-oxathiolane (BCH-1530), 2S-hydroxymethyl-4S-(5'-fluorocytosin-1'-yl)-1,3-oxathiolane (BCH-1529), 2R-hydroxymethyl-4S-(5'-fluorocytosin-1'-yl)-1,3-oxathiolane (BCH-1531), 2S-hydroxymethyl-4R-(5'-fluorocytosin-1'-yl)-1,3-oxathiolane (BCH-1528), and mixtures thereof;

and pharmaceutically acceptable salts and esters thereof in the form of a racemic mixture or single enantiomer.

10. The compound according to claim 9 selected from the group consisting of:

cis-2-hydroxymethyl-4-(cytosin-1'-yl)-1,3-oxathiolane (BCH-270) and cis-2-hydroxymethyl-4-(5'-fluorocytosin-1'-yl)-1,3-oxathiolane (BCH-1081);

and pharmaceutically acceptable salts and esters thereof in the form of a racemic mixture or single enantiomer.

11. The compound according to claim 10 selected from the group consisting of:

2R-hydroxymethyl-4R-(cytosin-1'-yl)-1,3-oxathiolane (BCH-1512);

2S-hydroxymethyl-4S-(cytosin-1'-yl)-1,3-oxathiolane (BCH-1533);

2R-hydroxymethyl-4R-(5'-fluorocytosin-1'-yl)-1,3-oxathiolane (BCH-1530); and 2S-hydroxymethyl-4S-(5'-fluorocytosin-1'-yl)-1,3-oxathiolane (BCH-1529); and pharmaceutically acceptable salts and esters thereof.

12. The compound according to claim 1 or claim 5 in the form of a racemic mixture.

13. The compound according to claim 1 or claim 5 substantially in the form of a single enantiomer.

14. A pharmaceutical formulation effective against viral infections comprising a pharmaceutically effective amount of a compound according to claim 1 or claim 5 and a pharmaceutically acceptable carrier.

15. An intermediate of formula (Ic), the geometric and optical isomers thereof, and mixtures of those isomers, useful for the production of substituted 1,3-oxathiolanes and substituted 1,3-dithiolanes with antiviral properties:

$$\text{RwOCH}_2 \underset{Y}{\overset{X}{\diagdown\diagup}} R_2 \quad (Ic)$$

wherein:

X is selected form the group consisting of S, S=O and SO$_2$;

Y is O;

R$_w$ is selected from the group consisting of silyl, C$_{1-6}$ alkyl, aralkyl, and C$_{1-6}$ acyl; and R$_2$ is selected from the group consisting of:

wherein x and y are independently O or S;

R$_3$ is selected from the group consisting of hydrogen, C$_{1-10}$ acyl, hydroxyl, amino, C$_{1-6}$ alkyl, C$_{2-6}$ alkenyl or alkynyl, and carboxyl;

R$_4$, R$_5$ and R$_6$ are independently selected from the group consisting of hydrogen, hydroxymethyl, trifluoromethyl, C$_{1-6}$ alkyl, C$_{2-6}$ alkenyl or alkynyl, bromine, chlorine, fluorine, iodine, hydroxyl, amino, cyano, carboxyl, carbamoyl, alkoxycarbonyl, arylthio, acyloxy, thiocarboxy, thiocarbamoyl, carbamate, ureido, amidino, aryloxy and carboxamide; and R$_7$ is selected from the group consisting of hydrogen, bromine, chlorine, fluorine, iodine, amino, hydroxyl, C$_{1-10}$ acyl, C$_{1-10}$ alkyl, and C$_{7-20}$ aralkyl.

16. The intermediate according to claim 15, wherein R$_2$ is selected from the group consisting of:

wherein:

R$_3$ is selected from the group consisting of hydrogen, C$_{1-10}$ acyl, hydroxyl, C$_{1-6}$ alkyl, C$_{2-6}$ alkenyl or alkynyl;

R$_4$ and R$_5$ are independently selected from the group consisting of hydrogen, hydroxymethyl, trifluoromethyl, C$_{1-6}$ alkyl, C$_{2-6}$ alkenyl or alkynyl, bromine, chlorine, fluorine, iodine, and arylthio;

R$_6$ is selected from the group consisting of hydrogen, bromine, chlorine, fluorine, iodine, cyano, carboxyl carboxamide, ethoxycarbonyl, carbamoyl, and thiocarbamoyl; and R$_7$ is selected from the group consisting of hydrogen, bromine, chlorine, fluorine, iodine, amino, and hydroxyl.

17. The intermediate according to claim 15 wherein R$_w$ is selected from the group consisting of benzyl, trityl, benzoyl and a benzoyl which may be substituted in any position by at least one group selected from the group consisting of bromine, chlorine, fluorine, iodine, C$_{1-6}$ alkyl, C$_{1-6}$ alkoxy, nitro and trifluoromethyl.

18. The intermediate according to claim 15 useful for the production of substituted 1,3-oxathiolanes with antiviral properties selected from the group consisting of:

cis-2-benzoyloxymethyl-4-(cytosin-1'-yl)-1,3-oxathiolane, trans-2-benzoyloxymethyl-4-(cytosin-1'-yl)-1,3-oxathiolane, and mixtures thereof;

cis-2-benzoyloxymethyl-4-(N4'-acetyl-cytosin-1'-yl)-1,3-oxathiolane, trans-2-benzoyloxymethyl-4-(N4'-acetylcytosin-1'-yl)-1,3-oxathiolane, and mixtures thereof;

cis-2-benzoyloxymethyl-4-(uracil-1'-yl)-1,3-oxathiolane, trans-2-benzoyloxymethyl-4-(uracil-1'-yl)-1,3-oxathiolane, and mixtures thereof;

cis-2-benzoyloxymethyl-4-(thymin-1'-yl)-1,3-oxathiolane, trans-2-benzoyloxymethyl-4-(thymin-1'-yl)-1,3-oxathiolane, and mixtures thereof;

cis-2-benzoyloxymethyl-4-(5'-fluorocytosin-1'-yl)-1,3-oxathiolane, trans-2-benzoyloxymethyl-4-(5'-fluorocytosin-1'-yl)-1,3-oxathiolane, and mixtures thereof;

2R-t-butyldiphenylsilyloxymethyl-4S-(N4'-acetylcytosin-1'-yl)-1,3-oxathiolane, 2R-t-butyldiphenylsilyloxymethyl-4R-(N4'-acetylcytosin-1'-yl)-1,3-oxathiolane, 2S-t-butyldiphenylsilyloxymethyl-4R-(N4'-acetylcytosin-1'-yl)-1,3-oxathiolane, 2S-t-butyldiphenylsilyloxymethyl-4S-(N4'-acetylcytosin-1'-yl)-1,3-oxathiolane, and mixtures thereof;

2R-t-butyldiphenylsilyloxymethyl-4S-(N4'-acetyl-5'-fluorocytosin-1'-yl)-1,3-oxathiolane, 2R-t-butyldiphenyl silyloxymethyl-4R-(N4'-acetyl-5'-fluorocytosin-1'-yl)-1,3-oxathiolane, 2S-t-butyldiphenylsilyloxymethyl-4R-(N4'-acetyl-5'-fluorocytosin-1'-yl)-1,3-oxathiolane, 2S-t-butyldiphenylsilyloxymethyl-4S-(N4'-acetyl-5'-fluorocytosin-1'-yl)-1,3-oxathiolane, and mixtures thereof.

\* \* \* \* \*

UNITED STATES PATENT AND TRADEMARK OFFICE
CERTIFICATE OF CORRECTION

PATENT NO. : 5,587,480
DATED : December 24, 1996
INVENTOR(S) : Belleau et al.

It is certified that error appears in the above-indentified patent and that said Letters Patent is hereby corrected as shown below:

On the title page,

"Other Publications"

| | |
|---|---|
| page 1, column 2, line 19 | where a comma -- , -- should be inserted after "al."; |
| page 1, column 2, line 22 | where a comma -- , -- should be inserted after "al."; |
| page 2, column 2, line 22 | where a comma -- , -- should be inserted after "al."; |
| page 2, column 2, line 25 | where a period -- . -- should be inserted after "al" |
| column 1, line 52 | where "Aced." should read -- Acad. -- ; |
| column 2, line 1 | where "el.," should read -- al.,-- ; |
| column 2, line 53 | where "HTV" should read -- HIV -- ; |
| column 2, line 56 | where "analogies" should read -- analogues --; |
| column 5, line 31 | where "verse" should read -- versa -- ; |

UNITED STATES PATENT AND TRADEMARK OFFICE
CERTIFICATE OF CORRECTION

PATENT NO. : 5,587,480
DATED : December 24, 1996
INVENTOR(S) : Belleau et al.

It is certified that error appears in the above-indentified patent and that said Letters Patent is hereby corrected as shown below:

| | |
|---|---|
| column 8, line 35 | where "1,3oxathiolanes" should read -- 1,3-oxathiolanes -- ; |
| column 8, line 42 | where the comma "," after "hydrogen" should be deleted; |
| column 11, line 58 | where a semicolon -- ; -- should be inserted after "thereof"; |
| column 11, line 64 | where a semicolon -- ; -- should be inserted after "thereof"; |
| column 15, line 29 | where a comma -- , -- should be inserted after "sugars"; |
| column 15, line 29 | where a comma -- , -- should be inserted after "Soc."; |
| column 15, line 29 | where a period -- . -- should be inserted after "pp"; |
| column 15, line 46 | where "Step4" should read -- Step 4 -- ; |
| column 15, line 57 | where -- the -- should be inserted after the first "of"; |
| column 16, line 51 | where "p." should read -- pp. -- ; |
| column 17, Scheme 2 (XXIV) | where "NH" should read -- $NH_2$ -- ; |

UNITED STATES PATENT AND TRADEMARK OFFICE
CERTIFICATE OF CORRECTION

PATENT NO. : 5,587,480
DATED : December 24, 1996
INVENTOR(S) : Belleau et al.

It is certified that error appears in the above-indentified patent and that said Letters Patent is hereby corrected as shown below:

| | |
|---|---|
| column 18, line 50 | where -- as -- should be inserted after "such"; |
| column 20, line 52 | where the "a" after "as" should be deleted; |
| column 27, line 46 | where "$C_2OCC_6H_5$" should read -- $CH_2OCC_6H_5$ --; |
| column 28, line 65 | where "$C_2OCC_6H_5$" should read -- $CH_2OCC_6H_5$ --; |
| column 29, line 50 | where "$C_6C_5COOCH_2$" should read -- $C_6H_5COOCH_2$ --; |
| column 30, line 15 | where the period "." after "$NHCOCH_3$" should read -- , --; |
| column 30, line 52 | where "$C_2O\underline{H}$" should read -- $CH_2O\underline{H}$ --; |
| column 31, line 3 | where "$C_2OH$" should read -- $CH_2OH$ --; |
| column 31, line 5 | where "$C_2OH$" should read -- $CH_2OH$ --; |
| column 31, line 53 | where "$C_2OH$" should read -- $CH_2OH$ --; |
| column 31, line 54 | where the comma "," after "(dd, 1H, $C_5$-H)" should read -- . --; |
| column 31, line 64 | where the comma "," after "(dd, 1H, $C_2$-$H_2$OBz)" should read -- . --; |

UNITED STATES PATENT AND TRADEMARK OFFICE
CERTIFICATE OF CORRECTION

PATENT NO. : 5,587,480
DATED : December 24, 1996
INVENTOR(S) : Belleau et al.

It is certified that error appears in the above-indentified patent and that said Letters Patent is hereby corrected as shown below:

| | |
|---|---|
| column 32, line 29 | where "$C_2OH$" should read -- $CH_2OH$ --; |
| column 32, line 32 | where the period "." after "$d_6$" should be deleted; |
| column 32, line 48 | where "$C_2OH$" should read -- $CH_2OH$ --; |
| column 32, line 50 | where "$C_2OH$" should read -- $CH_2OH$ --; |
| column 33, line 38 | where a comma -- , -- should be inserted after "(t, 1H, aromatic)"; |
| column 33, line 40 | where "$C_2OCC_6H_5$" should read -- $CH_2OCC_6H_5$ --; |
| column 33, line 40 | where a comma -- , -- should be inserted after the second "1H"; |
| column 34, line 10 | where "$C_2OH$" should read -- $CH_2OH$ --; |
| column 34, line 13 | where "$C_2OH$" should read -- $CH_2OH$ --; |
| column 34, line 30 | where "1.40" should read -- 11.40 --; |
| column 34, line 32 | where "$C_2OH$" should read -- $CH_2OH$ --; |
| column 34, line 34 | where "$C_2OH$" should read -- $CH_2OH$ --; |
| column 34, line 48 | where -- 1) -- should be inserted after "(example"; |

UNITED STATES PATENT AND TRADEMARK OFFICE
CERTIFICATE OF CORRECTION

PATENT NO. : 5,587,480
DATED : December 24, 1996
INVENTOR(S) : Belleau et al.

It is certified that error appears in the above-indentified patent and that said Letters Patent is hereby corrected as shown below:

| | |
|---|---|
| column 34, line 64 | where a comma -- , -- should be inserted after "$CH_2OOCC_6H_5$)"; |
| column 34, line 65 | where the comma "," after "($C_5$-H)" should read -- . --; |
| column 35, line 17 | where "with" after "poured" should be deleted; |
| column 35, line 28 | where a comma -- , -- should be inserted after "$C_2$-$CH_2OOCC_6H_5$)"; |
| column 36, line 1 | where a comma -- , -- should be inserted after "$C_2$-$CH_2OOCC_6H_5$)"; |
| column 36, line 38 | where "as" should be deleted; |
| column 36, line 40 | where -- the -- should be inserted after "in"; |
| column 37, line 12 | where a comma -- , -- should be inserted after "$C_2$-$CH_2OOCC_6H_5$"; |
| column 37, line 19 | where "$CH_2OOCC_6C_5$" should read -- $CH_2OOCC_6H_5$ --; |
| column 37, line 56 | where -- 90% -- should be inserted before "yield"; |
| column 37, line 59 | where a period -- . -- should be inserted after "nm"; |

UNITED STATES PATENT AND TRADEMARK OFFICE
CERTIFICATE OF CORRECTION

PATENT NO. : 5,587,480
DATED : December 24, 1996
INVENTOR(S) : Belleau et al.

It is certified that error appears in the above-indentified patent and that said Letters Patent is hereby corrected as shown below:

| | |
|---|---|
| column 37, line 65 | where the comma "," after "CH$_2$OH)" should read -- . --; |
| column 38, line 3 | where -- -2 -- should be inserted after "TRANS"; |
| column 40, line 3 | where a period -- . -- should be inserted after "(dec.)"; |
| column 40, line 4 | where a period -- . -- should be inserted after "4:1)"; |
| column 40, line 5 | where a period -- . -- should be inserted after "nm"; |
| column 43, line 5 | where "2.78" should read -- 7.78 --; |
| column 43, line 20 | where "1.35 g" should read -- 1.35g --; |
| column 43, line 28 | where "10" after "6 h" should be deleted; |
| column 44, line 1 | where "dired" should read -- dried --; |
| column 44, line 4 | where "seperation" should read -- separation --; |
| column 44, line 37 | where -- mixture of cis and trans 2S-t-butyldiphenylsiloxymethyl-4- -- should be inserted after "and"; |
| column 44, line 43 | where "dired" should read -- dried --; |

UNITED STATES PATENT AND TRADEMARK OFFICE
CERTIFICATE OF CORRECTION

PATENT NO. : 5,587,480
DATED : December 24, 1996
INVENTOR(S) : Belleau et al.

It is certified that error appears in the above-indentified patent and that said Letters Patent is hereby corrected as shown below:

| | |
|---|---|
| column 45, line 63 | where -- an -- should be inserted after "half"; |
| column 45, line 18 | where -- an -- should be inserted after "half"; |
| column 46, line 13 | where -- (BCH-1512) -- should be inserted after "1,3-OXATHIOLANE"; |
| column 46, line 39 | where "Et20MeOH" should read -- $Et_2OMeOH$ --; |
| column 46, line 50 | where -- (BCH-1533) -- should be inserted after "1,3-OXATHIOLANE"; |
| column 47, line 11 | where -- 4.6$H_z$), 4.38 (d, 1H, J=10.6$H_z$), 5.17 (t, 1H, J=4.5$H_z$), -- should be inserted after "J=10.6,"; |
| column 47, line 14 | where "DHSO-$d_6$" should read -- $DMSO-d_6$ --; |
| column 47, line 22 | where -- (BCH-1511) -- should be inserted after "1,3-OXATHIOLANE"; |
| column 47, line 60 | where -- (BCH-1532) -- should be inserted after "1,3-OXATHIOLANE"; |
| column 48, line 22 | where "J=S.7$H_z$" should read -- $J=5.7H_z$ --; |
| column 48, line 48 | where "0" after "1M" should be deleted; |

UNITED STATES PATENT AND TRADEMARK OFFICE
CERTIFICATE OF CORRECTION

PATENT NO. : 5,587,480
DATED : December 24, 1996
INVENTOR(S) : Belleau et al.

It is certified that error appears in the above-indentified patent and that said Letters Patent is hereby corrected as shown below:

| | |
|---|---|
| column 48, line 63 | where "1H" should read -- $^1H$ --; |
| column 49, line 26 | where -- an -- should be inserted after "half"; |
| column 49, line 42 | where -- (BCH-1531) -- should be inserted after "1,3-OXATHIOLANE"; |
| column 50, line 33 | where -- an -- should be inserted after "half"; |
| column 51, line 14 | where a comma -- , -- should be inserted after "0°C."; |
| column 52, line 32 | where "Ammomia" should read -- Ammonia --; |
| column 52, line 43 | where "6" should read -- δ --; |
| column 53, line 53 | where "mol" should read -- M.O.I. --; |
| column 54, line 38 | where "0.002-0.005" should read -- 0.002-0.05 --; |
| column 55, line 8 | where "CMBCs" should read -- CBMCs --; |
| column 56, line 38 (Claim 1) | where the semicolon ";" after "hydroxymethyl" should read -- , --; |
| column 57, line 34 (claim 3) | where "5" should read -- 2 --; |

UNITED STATES PATENT AND TRADEMARK OFFICE
CERTIFICATE OF CORRECTION

PATENT NO.  : 5,587,480
DATED       : December 24, 1996
INVENTOR(S) : Belleau et al.

It is certified that error appears in the above-indentified patent and that said Letters Patent is hereby corrected as shown below:

| | |
|---|---|
| column 58, line 25 (Claim 6) | where "$R_4$," should read -- $R_4$ --; |
| column 59, line 43 (Claim 15) | where "form" should read -- from --; |
| column 62, lines 15-16 (Claim 18) | where "butyldiphenyl silyloxymethyl" should read -- butyldiphenylsilyloxymethyl --; |

Signed and Sealed this

Fifth Day of August, 1997

Attest:

BRUCE LEHMAN

*Attesting Officer*   *Commissioner of Patents and Trademarks*